United States Patent

Matsumoto et al.

[11] Patent Number: 5,877,333
[45] Date of Patent: Mar. 2, 1999

[54] 1,2-DIOXETANE DERIVATIVES

[75] Inventors: Masakatsu Matsumoto, Sagamihara; Nobuko Watanabe, Kamakura; Hisako Kobayashi, Sagamihara; Hiroshi Ikawa, Tokyo, all of Japan

[73] Assignee: Fujirebio Inc., Tokyo, Japan

[21] Appl. No.: 964,680

[22] Filed: Nov. 5, 1997

Related U.S. Application Data

[62] Division of Ser. No. 753,788, Dec. 2, 1996, Pat. No. 5,731,445.

[30] Foreign Application Priority Data

Dec. 4, 1995 [JP] Japan .................................. 7-337717

[51] Int. Cl.⁶ .................................................. C07D 307/28
[52] U.S. Cl. ........................... 549/507; 549/497; 549/504
[58] Field of Search ..................................... 549/497, 504, 549/507, 464

[56] References Cited

U.S. PATENT DOCUMENTS 5,731,445  3/1998  Matsumoto et al. ..................... 549/464

*Primary Examiner*—Ba K. Trinh
*Attorney, Agent, or Firm*—Cooper & Dunham LLP

[57] ABSTRACT

A compound having the structure:

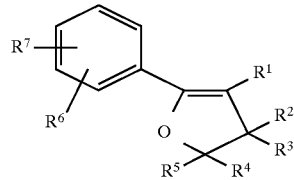

wherein $R^1$, $R^2$, $R^3$, $R^4$, and $R^5$ are each independently a hydrogen atom, an alkyl group or an aryl group, or wherein $R^2$ and $R^3$ together and $R^4$ and $R^5$ together are joined as a cycloalkyl group; wherein $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom, a halogen atom, an alkyl group, or an alkoxyl group.

15 Claims, 1 Drawing Sheet

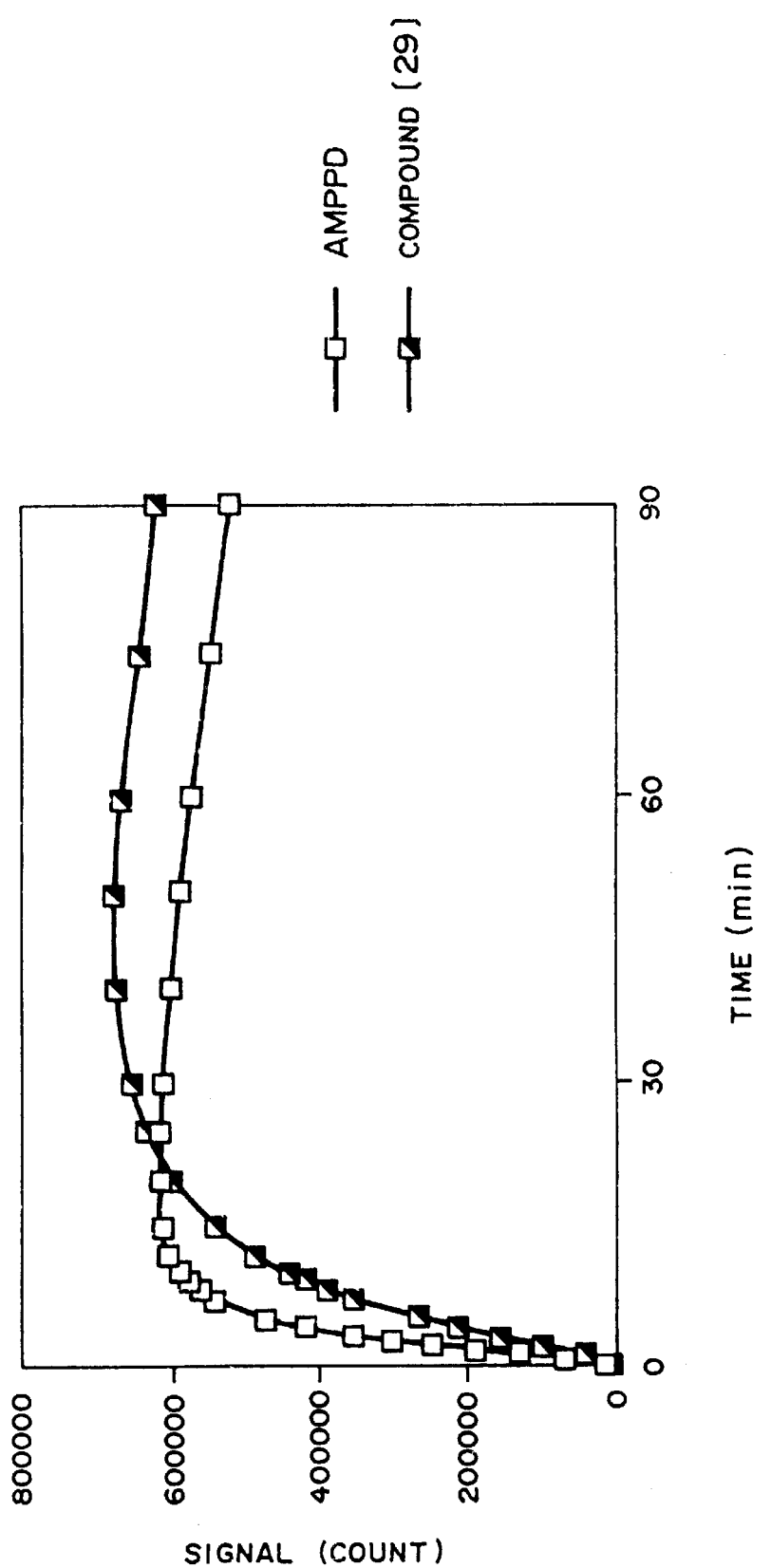

1,2-DIOXETANE DERIVATIVES

This is a division of application Ser. No. 08/753,788 filed Dec. 2, 1996 now U.S. Pat. No. 5,731,495.

BACKGROUND OF THE INVENTION

Japanese Patent Application No. 7-337717, filed Dec. 4, 1995, is hereby incorporated by reference.

1. Field of the Invention

The present invention relates to 1,2-dioxetane derivatives which can be used, for instance, as chemiluminescent reagents for immunoassays.

2. Discussion of Background

Conventionally, varieties of 1,2-dioxetane compounds have been synthesized, in particular, 1,2-dioxetane compounds substituted with a spiroadamantyl group at the 3 position thereof are known to be useful as chemiluminescent substrates, for instance, as disclosed in Japanese Patent Publications 5-21918 and 5-45590.

However, such conventional 1,2-dioxetane compounds cannot be said to be sufficiently thermally stable for use in practice, so that there has been a demand for an improved chemiluminescent compound.

SUMMARY OF THE INVENTION

It is therefore an object of the present invention to provide a chemiluminescent 1,2-dioxetane derivative which is sufficiently thermally stable for use in practice.

This object of the present invention can be achieved by a 1,2-dioxetane derivative of formula (I):

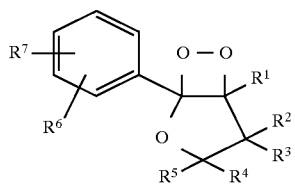

(I)

wherein $R^1$, $R^2$, $R^3$, $R^4$, and $R^5$ are each independently a hydrogen atom, an alkyl group or an aryl group, $R^2$ and $R^3$ together and $R^4$ and $R^5$ together can be joined as a cycloalkyl group, $R^6$ is a hydroxyl group, an alkoxyl group, an aralkyloxy group, —OSi($R^8$ $R^9$ $R^{10}$) in which $R^8$, $R^9$ and $R^{10}$ are each independently an alkyl group, or a phosphate salt group, and $R^7$ is a hydrogen atom, a halogen atom, an alkyl group or an alkoxyl group.

BRIEF DESCRIPTION OF THE DRAWINGS

In the drawing,

FIG. 1 is a graph showing the chemiluminescence of 5-t-butyl-4,4-dimethyl-1-(3'-phosphoryloxy)phenyl-2,6,7-trioxabicyclo[3.2.0]heptane disodium salt (Compound [29]) synthesized in Example 7 of the present invention in comparison with the chemiluminescence of a commercially available AMPPD (3-(2'-spiroadamantan)-4-methoxy-(3"-phosphoryloxy)phenyl- 1,2-dioxetane disodium salt).

DESCRIPTION OF THE PREFERRED EMBODIMENTS

The 1,2-dioxetane derivative of formula (I) of the present invention,

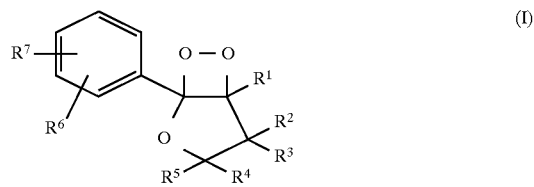

(I)

wherein $R^1$, $R^2$, $R^3$, $R^4$, and $R^5$ are each independently a hydrogen atom, an alkyl group or an aryl group, $R^2$ and $R^3$ together and $R^4$ and $R^5$ together can be joined as a cycloalkyl group, $R^6$ is a hydroxyl group, an alkoxyl group, an aralkyloxy group, —OSi($R^8$ $R^9$ $R^{10}$) in which $R^{8,}$ $R^9$ and $R^{10}$ are each independently an alkyl group, or a phosphate salt group, and $R^7$ is a hydrogen atom, a halogen atom, an alkyl group, or an alkoxyl group, can be synthesized in accordance with the following reaction scheme:

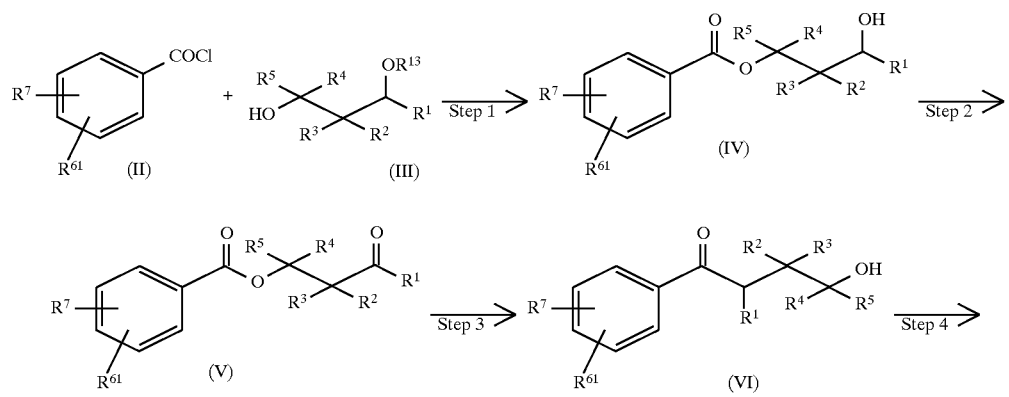

-continued

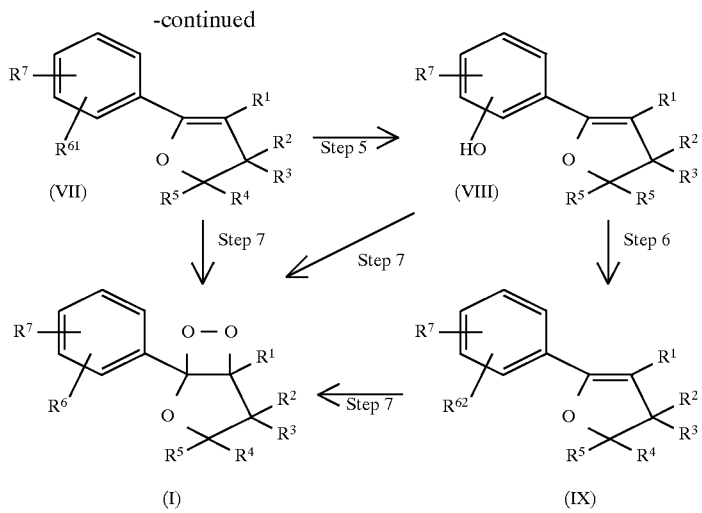

(VII)

(VIII)

Step 5

Step 7

Step 7

Step 6

(I)

Step 7

(IX)

wherein $R^1$ to $R^7$ are respectively the same as defined above, and $R^{13}$ is a hydrogen atom or a protective group for hydroxyl group, $R^{61}$ is an alkoxyl group or an aralkyloxy group, and $R^{62}$ is —$OSi(R^8\ R^9\ R^{10})$ in which $R^8$, $R^9$ and $R^{10}$ are each independently an alkyl group, or a phosphate salt group.

In the description of the present invention, the term "alkyl group" means a straight chain alkyl group having 1 to 20 carbon atoms, a branched alkyl group having 3 to 20 carbon atoms, each of which may have a substituent.

Examples of the alkyl groups are methyl group, ethyl group, propyl group, butyl group, pentyl group, hexyl group, heptyl group, octyl group, nonyl group, decyl group, undecyl group, dodecyl group, tridecyl group, tetradecyl group, pentadecyl group, hexadecyl group, heptadecyl group, octadecyl group, nonadecyl group and icosanyl group, which may be unbranched or branched.

Examples of the substituent for the above-mentioned alkyl groups are hydroxyl group, an alkoxyl group, an aryl group and a heterocyclic group.

Examples of the alkoxyl group are methoxy group, ethoxy group, propoxy group, butoxy group, pentyloxy group, hexyloxy group, methoxyethoxy group, methoxypropoxy group, ethoxyethoxy group, ethoxypropoxy group, and methoxyethoxyethoxy group.

Examples of the aryl group are phenyl group and naphthyl group.

Examples of the heterocyclic group are furyl group, thienyl group and pyridyl group.

Furthermore, in the present invention, the term "alkoxyl group" means an alkoxyl group having 1 to 20 carbon atoms, specific examples of which may be the same as mentioned above.

Furthermore, in the present invention, the term "aryl group" are aromatic hydrocarbon groups such as phenyl group and naphthyl group, and heteroaryl groups which may contain nitrogen, oxygen and/or sulfur in the rings thereof.

In the present invention, the term "aralkyloxy group" means such groups as benzyloxy group, and phenethyloxy group.

Furthermore, in the present invention, the term "halogen atom" means such halogen atoms as fluorine, chlorine, and bromine.

(Step 1)

In this step, an acid chloride of general formula (II) is allowed to react with an alcohol derivative of formula (III) in the presence of an amine such as pyridine or triethyl amine to produce an ester derivative of formula (IV-1):

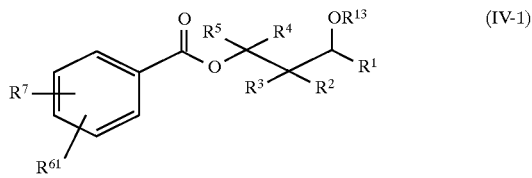

wherein $R^1$ to $R^5$, $R^7$ and $R^{61}$ are respectively the same as defined above, and $R^{13}$ is a hydrogen atom or a protective group for hydroxyl group, and when $R^{13}$ is a protective group for hydroxyl group, an alcohol derivative of general formula (IV) is produced after the deprotection is carried out.

(Step 2)

In this step, the alcohol derivative of general formula (IV) is oxidized in a halogenated hydrocarbon solvent such as dichloromethane in the presence of a chromium-based oxidizing agent, such as PCC or PDC, or in a combination of an activator and a solvent, such as Py.$SO_3$/triethylamine/DMSO or $Ac_2O$/DMSO, whereby a ketone derivative of general formula (V) is produced.

(Step 3)

In this step, the ketone derivative of general formula (V) is reduced to an alcohol derivative of general formula (VI), using a reducing agent and a base, in the presence of titanium. In this reaction, the use of titanium is indispensable. As a source for titanium, titanium halide such as titanium chloride is employed.

In the above reduction reaction, it is preferable that as the reducing agent, for example, lithium aluminum halide be employed, and as the base, for example, triethylamine or pyridine be employed to produce a reduction state.

It is preferable that the reaction be carried out in an ether such as tetrahydrofuran. The reaction proceeds at temperatures of 0° to 100° C., but in view of the reaction operation and the reactivity of the reaction mixture, it is preferable that the reaction be carried out with the reaction mixture being refluxed in THF.

(Step 4)

In this step, the alcohol derivative of general formula (VI) is subjected to dehydrative cyclization in the presence of a catalyst, whereby a dihydrofuran derivative of general formula (VII) is produced. It is preferable that, for example, PPTS or p-toluenesulfonic acid be employed as the catalyst. As a solvent for the above reaction, for example, an aromatic hydrocarbon such as benzene, toluene or xylene, can be employed.

(Step 5)

In this step, the dihydrofuran derivative of general formula (VII) is subjected to a deprotection reaction, whereby a phenol derivative of general formula (VIII) is produced.

The compound subjected to the deprotection reaction is the above-mentioned dihydrofuran derivative of general formula (VII), in which $R^1$ to $R^5$ are the same as defined above, and $R^{61}$ is a protective group for hydroxyl group, which is preferably methoxy group, or benzyloxy group.

This deprotection reaction is conventionally well known to those skilled in this art, which may be carried out either by reacting therewith an anion of an alkylthiol, or by carrying out the hydration thereof, which may be appropriately selected dependent upon the group to be deprotected.

(Step 6)

In this step, for the formation of silyloxy group or phosphoric group, a halogenated trialkyl silane or a halogenated phosphate respectively corresponding thereto is allowed to react with the above-mentioned alcohol derivative of general formula (VIII), whereby a compound of general formula (IX) is produced:

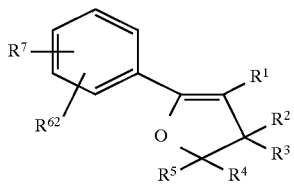

(IX)

wherein $R^1$ to $R^5$, and $R^7$ are the same as defined above, and $R^{62}$ is —$OSi(R^8 R^9 R^{10})$ in which $R^8$ to $R^{10}$ are the same as defined above, or

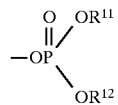

wherein $R^{11}$ and $R^{12}$ are each independently an alkyl group, or $R^{11}$ and $R^{12}$ together can be joined to form a ring.

In this step, when chloroethylene phosphate is reacted for the introduction of the phosphoric group, the chloroethylene is converted into a sodium salt of cyanoethylphosphate by use of sodium cyanide, followed by the elimination of a cyanoethyl group, and then converted into an ammonium sodium salt. The ammonium sodium salt can be easily converted into a disodium salt by reacting with sodium hydrogencarbonate.

(Step 7)

In this step, the dihydrofuran derivative of general formula (VII), general formula (VIII) or general formula (IX) is allowed to react with singlet oxygen, whereby the above-mentioned 1,2-dioxetane derivative of general formula (I) is produced.

The reaction of the dihydrofuran derivative of general formula (VII), general formula (VIII) or general formula (IX) with singlet oxygen can be carried out by dissolving the dihydrofuran derivative in a solvent, for example, a halogenated hydrocarbon such as dichloromethane, dichloroethane or carbon tetrachloride, or an alcohol such as methanol or ethanol, and irradiating the solution to visible light in the presence of a photosensitizer such as Methylene Blue, Rose Bengale or tetraphenylporphine in an atmosphere of oxygen. This reaction is carried out at −80° C. to room temperature.

The 1,2-dioxetane derivative of formula (I) may be a 1,2-dioxetane derivative of the following formula (Ia):

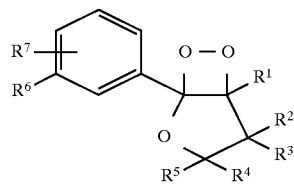

(Ia)

wherein $R^1$, $R^2$, $R^3$, $R^4$, and $R^5$ are each independently a hydrogen atom, an alkyl group, or an aryl group, $R^2$ and $R^3$ together and $R^4$ and $R^5$ together can be joined as a cycloalkyl group, $R^6$ is a hydroxyl group, an alkoxyl group, an aralkyloxy group, —$OSi(R^8 R^9 R^{10})$ in which $R^8$, $R^9$ and $R^{10}$ are each independently an alkyl group, or a phosphate salt, and $R^7$ is a hydrogen atom, a halogen atom, an alkyl group, or an alkoxyl group, as defined in the above-mentioned formula (I).

In the above 1,2-dioxetane derivative of formula (Ia), $R^1$, $R^2$ and $R^3$ may be each independently an alkyl group, $R^4$ may be an aryl group, $R^5$ may be a hydrogen atom, $R^6$ may be a hydroxyl group, an alkoxyl group, an aralkyloxy group, —$OSi(R^8 R^9 R^{10})$ in which $R^8$, $R^9$ and $R^{10}$ are each independently an alkyl group, or a phosphate salt, and $R^7$ may be a hydrogen atom.

In the above-mentioned 1,2-dioxetane derivative, $R^1$, $R^2$ and $R^3$ may be each independently an alkyl group having 1 to 4 carbon atoms, $R^4$ may be a phenyl group, $R^5$ may be a hydrogen atom, $R^6$ may be a hydroxyl group, an alkoxyl group which may be, for example, an alkoxyl group having 1 to 4 carbon atoms, —$OSi(R^8 R^9 R^{10})$ in which $R^8$, $R^9$ and $R^{10}$ are each independently an alkyl group which may be, for example, an alkyl group having 1 to 4 carbon atoms, or a phosphate salt, and $R^7$ is a hydrogen atom.

Furthermore, in the 1,2-dioxetane derivative of formula (Ia), $R^1$, $R^2$, $R^3$ and $R^4$ may be each independently an alkyl group, $R^5$ is a hydrogen atom, $R^6$ is a hydroxyl group, an alkoxyl group, an aralkyloxy group, —$OSi(R^8 R^9 R^{10})$ in which $R^8$, $R^9$ and $R^{10}$ are each independently an alkyl group, or a phosphate salt, and $R^7$ is a hydrogen atom.

In the above-mentioned 1,2-dioxetane derivative, $R^1$, $R^2$, $R^3$ and $R^4$ may be each independently an alkyl group having 1 to 4 carbon atoms, $R^5$ may be a hydrogen atom, $R^6$ may be a hydroxyl group, an alkoxyl group which may be, for example, an alkoxyl group having 1 to 4 carbon atoms, an aralkyloxy group, —$OSi(R^8 R^9 R^{10})$ in which $R^8$, $R^9$ and $R^{10}$ are each independently an alkyl group which may be, for example, an alkyl group having 1 to 4 carbon atoms, or a phosphate salt, and $R^7$ may be a hydrogen atom.

Other features of this invention will become apparent in the course of the following description of exemplary embodiments, which are given for illustration of the invention and are not intended to be limiting thereof.

Reference Example 1

(3-hydroxy-4-methyl)pentyl 3-methoxybenzoate (Compound [2])

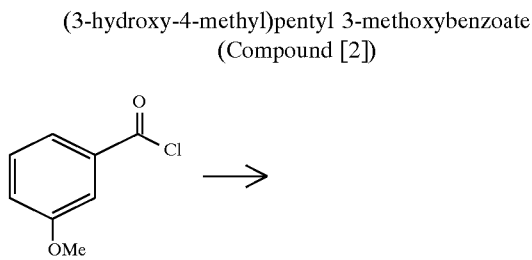

1.33 g (11.3 mmol) of 4-methyl-1,3-pentanediol and 1.80 ml (22.3 mmol) of pyridine were dissolved in 20 ml of 1,2-dichloroethane. The solution was stirred in an atmosphere of argon at 0° C.

To this solution, a solution of 1.60 ml (11.4 mmol) of m-anisoyl chloride (Compound [1]) in 15 ml of 1,2-dichloroethane was added dropwise over a period of 30 minutes, and the mixture was then stirred for 1 hour.

This reaction mixture was poured into a saturated aqueous solution of sodium chloride. The mixture was then extracted with ethyl acetate. The ethyl acetate extract layer was washed with a saturated aqueous solution of sodium chloride, dried over magnesium sulfate, and concentrated.

The residue was chromatographed on silica gel, and eluted with a mixed solvent of chloroform and ethyl-acetate (100:1), whereby (3-hydroxy-4-methyl)pentyl 3-methoxybenzoate (Compound [2]) was obtained in the form of a colorless oil in a yield of 2.33 g (81.2%).

$^1$HNMR (300 MHz, CDCl$_3$): δ0.95 (d, J=6.8 Hz, 6H), 1.65–1.85 (m, 2H), 1.90–2.04 (m, 2H), 3.48–3.59 (m, 1H), 3.86 (s, 3H), 4.43 (ddd, J=11.1, 6.0 and 5.1 Hz, 1H), 4.60 (ddd, J=11.1, 8.8 and 5.3 Hz, 1H), 7.11 (ddd, J=8.3, 2.6 and 0.8 Hz, 1H), 7.35 (dd, J=8.3 and 7.7 Hz, 1H), 7.56 (dd, J=2.6 and 1.5 Hz, 1H), 7.63 (d with fine coupling, J=7.7 Hz, 1H) ppm IR (liq. film): 3524, 2964, 1722, 1602, 1588, 1468, 1282, 1108, 1046 cm$^{-1}$, Mass (m/z, %): 252 (M$^+$, 12), 209 (10), 153 (15), 152 (30), 135 (100), 107 (13), 100 (14), 77 (10)

Reference Example 2

(4-methyl-3-oxo)pentyl 3-methoxybenzoate (Compound [3])

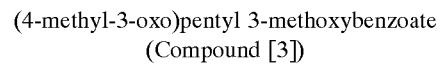

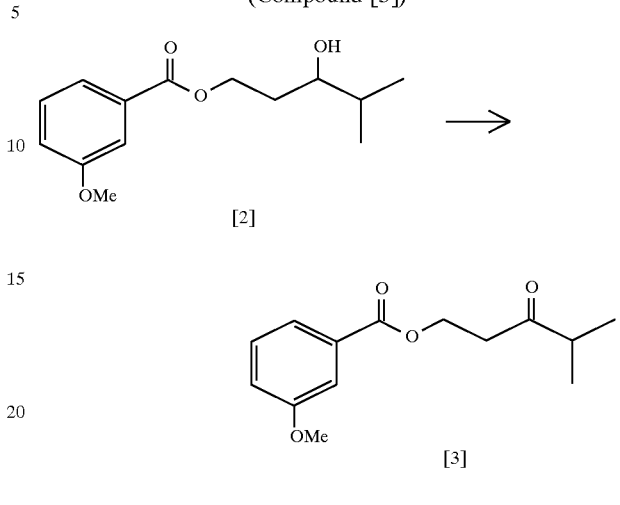

2.14 g (8.49 mmol) of the compound [2] synthesized in Reference Example 1 and 6.1 g of celite were added to 40 ml of dichloromethane. The mixture was stirred in an atmosphere of argon at room temperature.

To this mixture, 2.0 g (9.28 mmol) of pyridinium chlorochromate was added, and the mixture was stirred for 4 hours.

To this reaction mixture, diethyl ether was added. The mixture was filtered through celite, and concentrated.

The residue was chromatographed on silica gel and eluted with a mixed solvent of hexane and ethyl acetate (3:1), whereby (4-methyl-3-oxo)pentyl 3-methoxybenzoate (Compound [3]) was obtained in the form of a colorless oil in a yield of 1.811 g (85.3%).

$^1$HNMR (300 MHz, CDCl$_3$): δ1.14 (d, J=6.9 Hz, 6H), 2.65 (sept, J=6.9 Hz, 1H), 2.92 (t, J=6.4 Hz, 2H), 3.84 (s, 3H), 4.60 (t, J=6.4 Hz, 2H), 7.09 (ddd, J=8.3, 2.7 and 0.9 Hz, 1H), 7.33 (dd, J=8.3 and 7.6 Hz, 1H), 7.52 (s with fine coupling, 1H), 7.58 (d with fine coupling, J=7.6 Hz, 1H) ppm IR(liq. film): 2972, 1724, 1602, 1588, 1490, 1280 cm$^{-1}$ Mass (m/z, %): 250 (M$^+$, 27), 135 (100), 107 (11), 92 (10)

Reference Example 3

3-(3-methoxy)benzoyl-4-methylpentanol (Compound [4])

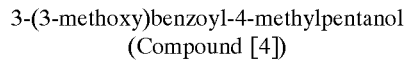

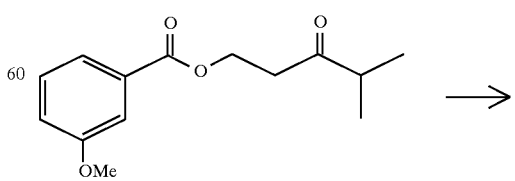

-continued

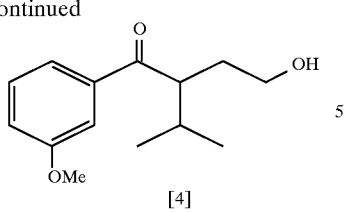

[4]

In an atmosphere of argon, 4.9 g (31.8 mmol) of titanium trichloride was suspended in 100 ml of anhydrous THF. This suspension was stirred for 15 minutes and then ice-cooled.

To this suspension, 620 mg (16.3 mmol) of lithium aluminum hydride was added thereto under ice cooling. The mixture was then stirred at room temperature for 40 minutes.

To this solution, 2.3 ml (16.5 mmol) of triethylamine was added, and the mixture was refluxed for 30 minutes.

To this mixture, there was added dropwise over a period of 20 minutes a solution of 817 mg (32.7 mmol) of the compound [3] synthesized in Reference Example 2 in 30 ml of anhydrous THF, and the mixture was further refluxed for 1 hour.

The reaction mixture was poured into iced water, and the mixture was then extracted with ethyl acetate.

The ethyl acetate extract layer was successively washed with water, an aqueous solution of sodium hydrogencarbonate, and a saturated aqueous solution of sodium chloride, dried over magnesium sulfate, and then concentrated.

The residue was chromatographed on silica gel and eluted with a mixed solvent of hexane and dichloromethane (10:1), whereby 3-(3-methoxy)benzoyl-4-methylpentanol (compound [4]) was obtained in the form of a colorless oil in a yield of 450 mg (58.3%).

$^1$HNMR (300 MHz, CDCl$_3$): δ0.90 (d, J=6.8 Hz, 3H), 0.96 (d, J=6.8 Hz, 3H), 1.29 (t, J=5.2 Hz, 1H), 1.75–1.88 (m, 1H), 1.97–2.20 (m, 2H), 3.40–3.70 (m, 3H), 3.86 (s, 3H), 7.11 (ddd, J=8.2, 2.7 and 0.9 Hz, 1H), 7.38 (dd, J=8.2 and 7.7 Hz, 1H), 7.51 (s with fine coupling, 1H), 7.56 (d with fine coupling, J=7.7 Hz, 1H) ppm IR (liq. film): 3488, 2964, 1680, 1598, 1582, 1432, 1260, 1046 cm$^{-1}$ Mass (m/z, %): 236 (M$^+$, 12), 192 (25), 152 (11), 136 (10), 135 (100), 107 (13)

Reference Example 4

4-isopropyl-5-(3-methoxy)phenyl-2,3-dihydrofuran (Compound [5])

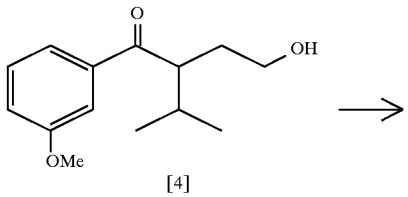

[4]

-continued

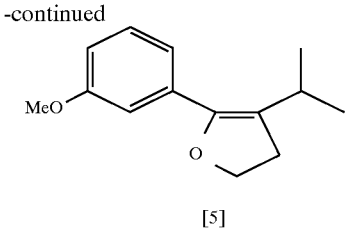

[5]

903 mg (3.83 mmol) of the compound [4] synthesized in Reference Example 3 was dissolved in 50 ml of anhydrous toluene, and the solution was stirred in an atmosphere of argon at room temperature.

To this solution, there were added 315 mg (12.5 mmol) of pyridinium p-toluenesulfonate and 3.0 g (21.1 mmol) of sodium sulfate, and the mixture was stirred overnight.

This reaction mixture was poured into an aqueous solution of sodium hydrogencarbonate. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (10:1), whereby 4-isopropyl-5-(3-methoxy)phenyl-2,3-dihydrofuran (Compound [5]) was obtained in the form of a colorless oil in a yield of 183 mg (21.9%).

$^1$HNMR (300 MHz, CDCl$_3$): δ1.10 (d, J=6.8 Hz, 6H), 2.77 (t, J=9.4 Hz, 2H), 2.99 (sept, J=6.8 Hz, 1H), 3.82 (s, 3H), 4.35 (t, J=9.4 Hz, 2H), 6.84 (ddd, J=8.2, 2.6 and 0.8 Hz, 1H), 7.02 (s with fine coupling, 1H), 7.05 (d with fine coupling, J=7.7 Hz, 1H), 7.27 (dd, J=8.2 and 7.7 Hz, 1H) ppm IR (liq. film): 2964, 1600, 1580, 1212, 1040 cm$^{-1}$ Mass (m/z, %): 218 (M$^+$, 54), 204 (24), 203 (100), 135 (49), 107 (14), 92 (12)

EXAMPLE 1

5-isopropyl-1-(3-methoxy)phenyl-2,6,7-trioxabicyclo[3.2.0]heptane (Compound [6])

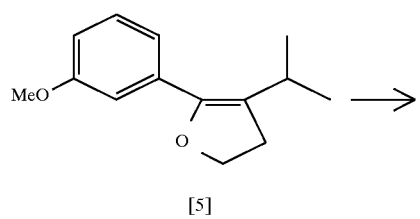

[5]

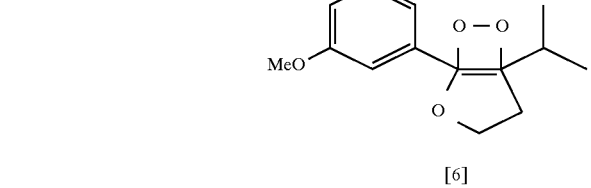

[6]

80 mg (0.37 mmol) of the compound [5] synthesized in Reference Example 4 and 2 mg of TPP were dissolved in 20 ml of dichloromethane, and the solution was stirred in an atmosphere of oxygen at −78° C.

This solution was irradiated with a sodium lamp (180 W) for 3 hours. The reaction mixture was then concentrated.

The residue was chromatographed on silica gel and eluted with a mixed solvent of hexane and ethyl acetate (20:1 to 10:1), whereby 5-isopropyl-1-(3-methoxy)phenyl-2,6,7-trioxabicyclo[3.2.0]heptane (Compound [6]) was obtained in the form of an amorphous solid in a yield of 52 mg (56.7%).

$^1$HNMR (300 MHz, CDCl$_3$): δ0.40 (d, J=6.8 Hz, 3H), 0.84 (d, J=6.8 Hz, 3H), 2.03 (ddd, J=13.9, 11.1 and 7.9 Hz, 1H), 2.18 (dd, J=13.9 and 5.7 Hz, 1H), 2.40 (sept, J=6.8 Hz, 1H), 3.84 (s, 3H), 4.55 (dd, J=8.6 and 7.9 Hz, 1H), 4.79 (ddd, J=11.1, 8.6 and 5.7 Hz, 1H), 6.96 (d with fine coupling, J=6.8 Hz, 1H), 7.24–7.38 (m, 3H) ppm IR (KBr): 2972, 1612, 1586 cm$^{-1}$ Mass (m/z, %): 250 (M$^+$, 26), 218 (2), 207 (4), 203 (3), 135 (100)

Reference Example 5

(3-hydroxy-2,2,4-trimethyl)pentyl 3-methoxybenzoate (Compound [7])

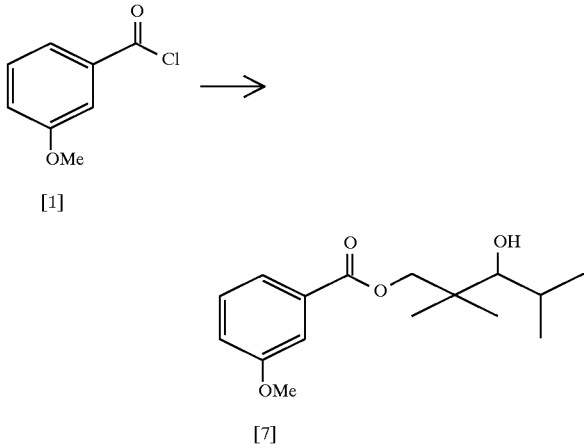

In an atmosphere of argon, 6.03 g (41.2 mmol) of 2,2,4-trimethyl-1,3-pentanediol and 5.20 ml (64.3 mmol) of pyridine were dissolved in 40 ml of 1,2-dichloroethane, and the solution was stirred at 0° C.

To this solution, 4.50 ml (32.0 mmol) of m-anisoyl chloride dissolved in 60 ml of 1,2-dichloroethane was added dropwise over a period of 1 hour, and the mixture was stirred for 40 minutes. This reaction mixture was further stirred at room temperature for 40 minutes.

The above-mentioned reaction mixture was poured into a saturated aqueous solution of sodium chloride. The mixture was then extracted with ethyl acetate. The ethyl acetate extract layer was washed with a saturated aqueous solution of sodium chloride, dried over magnesium sulfate, and then concentrated.

The residue was chromatographed on silica gel and eluted successively with dichloromethane and then with a mixed solvent of dichloromethane and ethyl acetate (7:1), whereby (3-hydroxy-2,2,4-trimethyl)pentyl 3-methoxybenzoate (Compound [7]) was obtained in the form of a colorless oil in a yield of 6.93 g (77.3%).

$^1$HNMR (300 MHz, CDCl$_3$): δ0.96 (d, J=6.8 Hz, 3H), 1.02 (d, J=7.0 Hz, 3H), 1.05 (s, 3H), 1.07 (s, 3H), 1.89 (d, J=6.2 Hz, 1H), 1.98 (sept d, J=6.8 and 2.4 Hz, 1H), 3.37 (dd, J=6.2 and 2.4 Hz, 1H), 3.86 (s, 3H), 4.01 (d, J=10.9 Hz, 1H), 4.38 (d, J=10.9 Hz, 1H), 7.12 (ddd, J=8.3, 2.6 and 0.9 Hz, 1H), 7.36 (dd, J=8.3 and 7.6 Hz, 1H), 7.56 (dd, J=2.6 and 1.6 Hz, 1H), 7.63 (d with fine coupling, J=7.6 Hz, 1H) ppm IR(liq. film): 3544, 2968, 1718, 1602, 1588, 1470, 1280, 1184 cm$^{-1}$ Mass (m/z, %): 280 (M$^+$, 4), 237 (7), 152 (100), 135 (75), 107 (11)

Reference Example 6

(2,2,4-trimethyl-3-oxo)pentyl 3-methoxybenzoate (Compound [8])

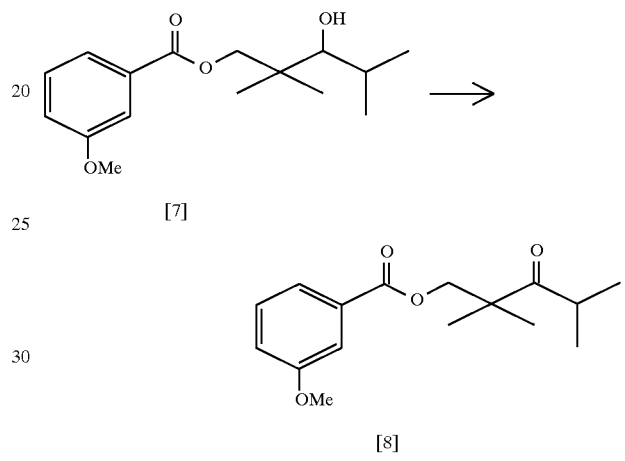

2.582 g (9.22 mmol) of the compound [7] synthesized in Reference Example 5 and 6.0 g of celite were added to 40 ml of dichloromethane, and the mixture was stirred in an atmosphere of argon at room temperature.

To this mixture, 2.20 g (10.2 mmol) of pyridinium chlorochromate was added, and the mixture was stirred for 3 hours.

To this mixture, 241 mg (0.993 mmol) of pyridinium chlorochromate was further added, and the mixture was stirred for 19 hours.

To this reaction mixture, diethyl ether was added. The mixture was filtered through celite, and concentrated.

The residue was chromatographed on silica gel and eluted with a mixed solvent of hexane and ethyl acetate (3:1), whereby (2,2,4-trimethyl-3-oxo)pentyl 3-methoxybenzoate (Compound [8]) was obtained in the form of a colorless oil in a yield of 2.407 g (93.9%).

$^1$HNMR (300 MHz, CDCl$_3$): δ1.08 (d, J=6.7 Hz, 6H), 1.28 (s, 6H), 3.16 (sept, J=6.7 Hz, 1H), 3.84 (s, 3H), 4.39 (s, 2H), 7.10 (ddd, J=8.3, 2.7 and 0.80 Hz, 1H), 7.33 (dd, J=8.3 and 7.6 Hz, 1H), 7.50 (s with fine coupling, 1H), 7.56 (d with fine coupling, J=7.6 Hz, 1H) ppm IR (liq. film): 2976, 1724, 1602, 1588, 1472, 1278, 1228 cm$^{-1}$ Mass (m/z, %): 278 (M$^+$, 9), 222 (42), 152 (48), 135 (100), 107 (14)

Reference Example 7

3-(3-methoxy)benzoyl-2,2,4-trimethylpentanol (Compound [9])

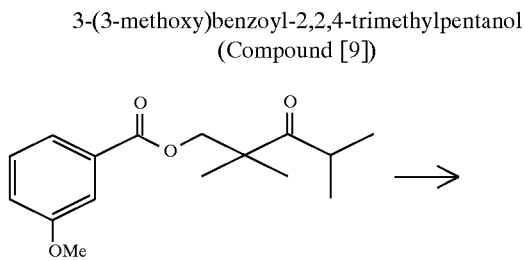

[8]

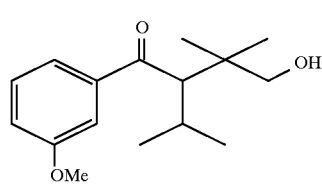

[9]

In an atmosphere of argon, 6.0 g (38.9 mmol) of titanium trichloride was suspended in 100 ml of anhydrous THF, and the suspension was stirred at room temperature for 20 minutes.

To the solution, 680 mg (17.9 mmol) of lithium aluminum hydride was added under ice cooling. The mixture was then stirred at room temperature for 30 minutes.

To this solution, 2.4 ml (17.2 mmol) of triethylamine was added, and the mixture was refluxed for 35 minutes.

To this reaction mixture, there was added dropwise over a period of 40 minutes a solution of 928 mg (3.34 mmol) of the compound [8] synthesized in Reference Example 6 in 20 ml of anhydrous THF, and the mixture was refluxed for 1 hour and 10 minutes.

This reaction mixture was poured into an aqueous solution of sodium hydrogencarbonate. The mixture was then extracted with ethyl acetate.

The ethyl acetate extract layer was successively washed with a saturated aqueous solution of sodium chloride and then with water, dried over magnesium sulfate, and then concentrated.

The residue was chromatographed on silica gel and eluted with a mixed solvent of hexane and ethyl acetate (4:1), whereby 3-(3-methoxy)benzoyl-2,2,4-trimethylpentanol (Compound [9]) was obtained in the form of an amorphous solid in a yield of 622 mg (70.6%).

The thus obtained 3-(3-methoxy)benzoyl-2,2,4-trimethylpentanol was used in the next reaction without further purification.

Reference Example 8

4-isopropyl-5-(3-methoxy)phenyl-3,3-dimethyl-2,3-dihydrofuran (Compound [10])

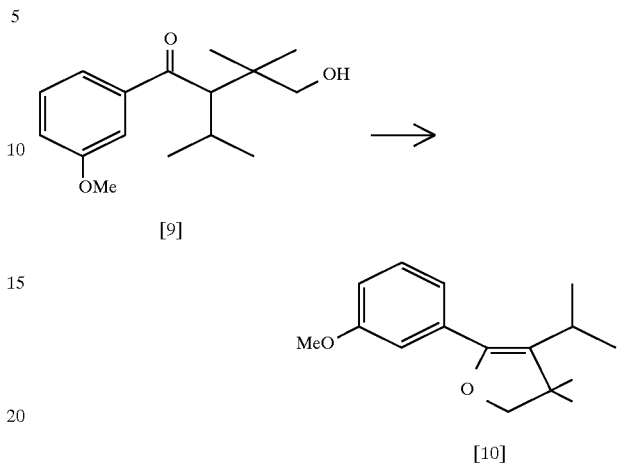

621 mg (2.35 mmol) of the compound [9] synthesized in Reference Example 7 was dissolved in 12 ml of 1,2-dichloroethane, and the solution was stirred in an atmosphere of argon at room temperature.

To this solution, 60 mg (0.239 mmol) of pyridinium p-toluenesulfonate was added, and the mixture was stirred for 2 hours.

This reaction mixture was poured into an aqueous solution of sodium hydrogencarbonate. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (10:1), whereby 4-isopropyl-5-(3-methoxy)phenyl-3,3-dimethyl-2,3-dihydrofuran (Compound [10]) was obtained in the form of a colorless oil in a yield of 471 mg (81.4%).

$^1$HNMR (300 MHz, CDCl$_3$): δ1.15 (d, J=7.2 Hz, 6H), 1.26 (s, 6H), 2.80 (sept, J=7.2 Hz, 1H), 3.82 (s, 3H), 3.39 (s, 2H), 6.85 (ddd, J=8.3, 2.7 and 0.9 Hz, 1H), 6.97 (s with fine coupling, 1H), 7.01 (d with fine coupling, J=7.6 Hz, 1H), 7.26 (dd, J=8.3 and 7.6 Hz, 1H) ppm IR (liq. film): 2964, 1600, 1588, 1466, 1230, 1048 cm$^{-1}$ Mass (m/z, %): 246 (M$^+$, 31), 232 (16), 231 (100), 189 (28), 135 (27)

EXAMPLE 2

5-isopropyl-1-(3-methoxy)phenyl-4,4-dimethyl-2,6,7-trioxabicyclo[3.2.0.]heptane (Compound [11])

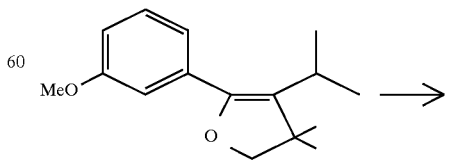

[10]

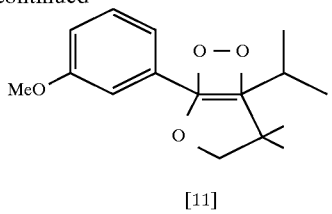

[11]

50 mg (0.203 mmol) of the compound [10] synthesized in Reference Example 8 and 3 mg of TPP were dissolved in 20 ml of dichloromethane, and the solution was stirred in an atmosphere of oxygen at −78° C.

This solution was irradiated with a sodium lamp (180 W) for 3 hours.

The reaction mixture was then concentrated. The residue was chromatographed on silica gel and eluted successively with a mixed solvent of hexane and dichloromethane (4:1 to 2:1 to 1:1), whereby 5-isopropyl-1-(3-methoxy)phenyl-4,4-dimethyl-2,6,7-trioxabicyclo[3.2.0]heptane (Compound [11]) was obtained in the form of a colorless oil in a yield of 46 mg (81.4%).

$^1$HNMR (300 MHz, CDCl$_3$): δ0.75 (d, J=7.1 Hz, 3H), 0.90 (d, J=6.7 Hz, 3H), 1.16 (s, 3H), 1.24 (s, 3H), 2.15–2.31 (m, 1H), 3.83 (s, 3H), 3.88 (d, J=8.3 Hz, 1H), 4.57 (d with fine coupling, J=8.3 Hz, 1H), 6.93 (ddd, J=8.2, 2.6 and 0.9 Hz, 1H), 7.11 (s with fine coupling, 1H), 7.14 (d with fine coupling, J=7.7 Hz, 1H), 7.32 (dd, J=8.2 and 7.7 Hz, 1H) ppm IR (liq. film): 2972, 2892, 1604, 1588, 1234, 1046 cm$^{-1}$ Mass (m/z, %): 278 (M$^+$, 7), 246 (8), 231 (14), 222 (32), 152 (38), 135 (100)

Reference Example 9

5-(3-hydroxy)phenyl-4-isopropyl-3,3-dimethyl-2,3-dihydrofuran (Compound [12])

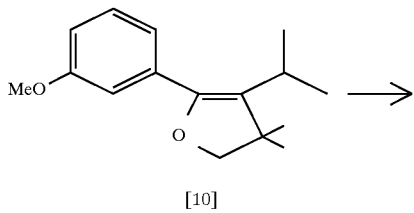

[10]

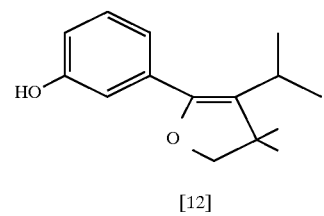

[12]

In an atmosphere of argon, 0.2 ml (2.70 mmol) of ethanethiol was added to a suspension prepared by dispersing 100 mg (2.50 mmol) of sodium hydride (60%) in 2.5 ml of anhydrous DMF, and the mixture was stirred for 20 minutes.

To this solution, there was added a solution of 246 mg (1.00 mmol) of the compound [10] synthesized in Reference Example 8 in 3.5 ml of anhydrous DMF, and the mixture was stirred at 130° C. for 3 hours.

This reaction mixture was poured into a saturated aqueous solution of sodium chloride. The mixture was then extracted with ethyl acetate. The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (6:1), whereby 5-(3-hydroxy)phenyl-4-isopropyl-3,3-dimethyl-2,3-dihydrofuran (Compound [12]) was obtained in the form of a colorless oil in a yield of 220 mg (94.8%).

$^1$HNMR (300 MHz, CDCl$_3$): δ1.15 (d, J=7.2 Hz, 6H), 1.26 (s, 6H), 2.81 (sept, J=7.2 Hz, 1H), 3.92 (s, 2H), 4.69 (s, 1H), 6.78 (ddd, J=8.1, 2.6 and 1.0 Hz, 1H), 6.90 (dd, J=2.6 and 1.5 Hz, 1H), 7.00 (d with fine coupling, J=7.7 Hz, 1H), 7.22 (dd, J=8.1 and 7.7 Hz, 1H) ppm IR (liq. film): 3416, 2964, 1582, 1448, 1310, 1224, 1036 cm$^{-1}$ Mass (m/z, %): 232 (M$^+$, 35), 218 (15), 217 (100), 175 (34), 121 (32)

Reference Example 10

5-(3-t-butyldimethylsiloxy)phenyl-4-isopropyl-3,3-dimethyl-2,3-dihydrofuran (Compound [13])

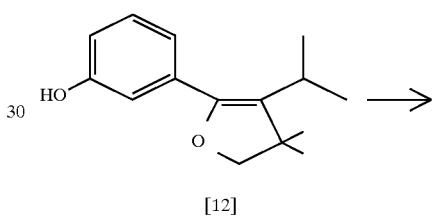

[12]

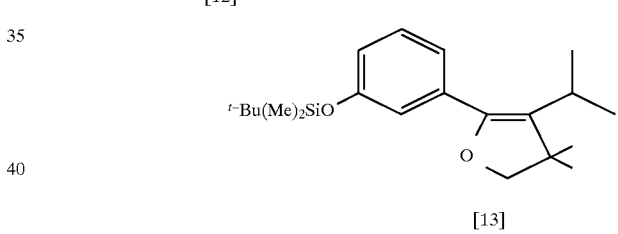

[13]

204 mg (0.879 mmol) of the compound [12] synthesized in Reference Example 9 was dissolved in 3 ml of anhydrous DMF, and the solution was stirred in an atmosphere of argon at room temperature.

To this solution, 133 mg (1.95 mmol) of imidazole and 270 mg (1.79 mmol) of t-butyldimethylchlorosilane were added, and the mixture was stirred overnight.

This reaction mixture was poured into water. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (20:1), whereby 5-(3-t-butyldimethylsiloxy)phenyl-4-isopropyl-3,3-dimethyl-2,3-dihydrofuran (Compound [13]) was obtained in the form of a colorless oil in a yield of 290 mg (95.3%).

$^1$HNMR (300 MHz, CDCl$_3$): δ0.19 (s, 6H), 0.98 (s, 9H), 1.14 (d, J=7.2 Hz, 6H), 1.25 (s, 6H), 2.79 (sept, J=7.2 Hz, 1H), 3.92 (s, 2H), 6.77 (ddd, J=8.1, 2.5 and 1.1 Hz, 1H), 6.90 (s with fine coupling, 1H), 7.02 (d with fine coupling, J=7.7 Hz, 1H), 7.19 (dd, J=8.1 and 7.7 Hz, 1H) ppm IR (liq. film): 2960, 1600, 1580, 1486, 1254 cm$^{-1}$ Mass (m/z, %): 346 (M$^+$, 22), 332 (27), 331 (100), 289 (14), 231 (14)

EXAMPLE 3

1-(3-t-butyldimethylsiloxy)phenyl-5-isopropyl-4,4-dimethyl-2,6,7-trioxabicyclo[3.2.0]heptane (Compound [14])

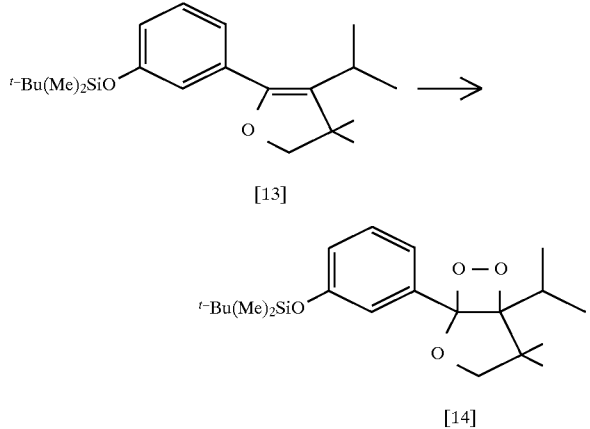

77 mg (0.223 mmol) of the compound [13] synthesized in Reference Example 10 and 2 mg of TPP were dissolved in 20 ml of dichloromethane, and the solution was stirred in an atmosphere of oxygen at −78° C.

This solution was irradiated with a sodium lamp (180 W) for 3 hours. The reaction mixture was then concentrated.

The residue was chromatographed on silica gel and eluted with a mixed solvent of hexane and ether (20:1), whereby 1-(3-t-butyldimethylsiloxy)phenyl-5-isopropyl-4,4-dimethyl-2,6,7-trioxabicylo[3.2.0]heptane (Compound [14]) was obtained in the form of a colorless oil in a yield of 71 mg (84.4%).

$^1$HNMR (300 MHz, CDCl$_3$): δ0.18 (s, 6H), 0.74 (d, J=7.1 Hz, 3H), 0.90 (d, J=6.7 Hz, 3H), 0.98 (s, 9H), 1.16 (s, 3H), 1.23 (s, 3H), 2.14–2.30 (m, 1H), 3.87 (d, J=8.3 Hz, 1H), 4.56 (d, J=8.3 Hz, 1H), 6.86 (d with fine coupling, J=8.0 Hz, 1H), 7.04 (s with fine coupling, 1H), 7.14 (d, J=7.6 Hz, 1H), 7.26 (dd, J=8.0 and 7.0 Hz, 1H) ppm IR (liq. film): 2964, 1606, 1588, 1256, 1004 cm$^{-1}$ Mass (m/z, %): 378 (M$^+$, 29), 346 (5), 322 (25), 292 (18), 291 (82), 266 (22), 265 (62), 235 (67), 222 (19), 221 (100), 179 (31), 150 (31), 135 (35)

Reference Example 11

3-(4-isopropyl-3,3-dimethyl-2,3-dihydrofuran-5-yl)phenylethylenephosphate (Compound [15])

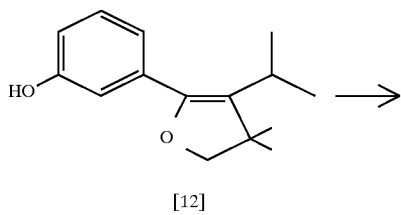

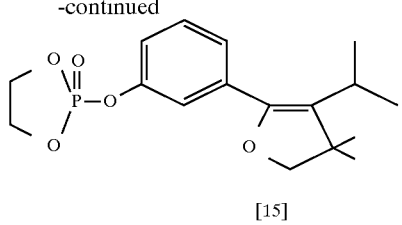

387 mg (1.67 mmol) of the compound [12] synthesized in Reference Example 9 was dissolved in 5 ml of anhydrous toluene, and the solution was stirred in an atmosphere of argon at 0° C.

To this solution, 0.28 ml (2.01 mmol) of triethylamine was added, and 0.154 ml (1.66 mmol) of 2-chloro-1,3,2-dioxaphosphoran-2-oxide was then added. The mixture was stirred at 0° C. for 40 minutes and then stirred at room temperature for 1 hour and 30 minutes.

This reaction mixture was concentrated. The residue was dissolved in ether. The solution was filtered. The filtrate was concentrated, whereby a crude 3-(4-isopropyl-3,3-dimethyl-2,3-dihydrofuran-5-yl)phenylethylenephosphate was obtained in the form of a colorless oil in a yield of 604 mg.

$^1$HNMR (300 MHz, CDCl$_3$): δ1.16 (d, J=7.1 Hz, 6H), 1.26 (s, 6H), 2.78 (sept, J=7.1 Hz, 1H), 3.93 (s, 2H), 4.18–4.34 (m, 2H), 4.40–4.56 (m, 2H) and 7.14–7.38 (m, 4H) ppm

Reference Example 12 ammonium sodium 3-(4-isopropyl-3,3-dimethyl-2,3-dihydrofuran-5-yl)phenylphosphate (Compound [16])

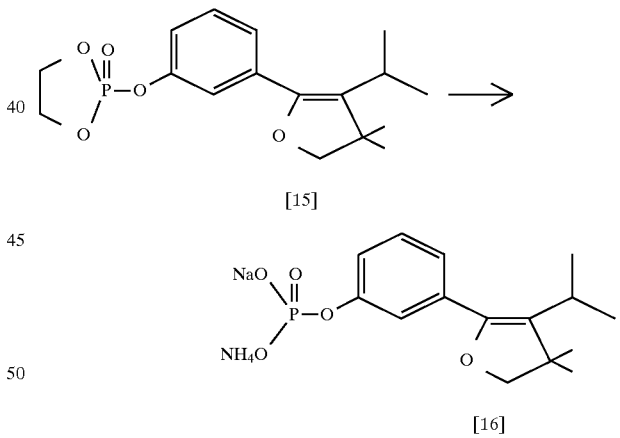

604 mg of the crude product of the compound [15] synthesized in Reference Example 11 was dissolved in 7 ml of anhydrous DMF, and the solution was stirred in an atmosphere of argon at room temperature.

To this solution, 95 mg (1.84 mmol) of sodium cyanide (95%) was added. The mixture was stirred overnight, and then concentrated.

The residue was dissolved in water, washed with hexane and subjected to freeze-drying, whereby 598 mg of an amorphous solid was obtained. 5 ml of ammonia water (28%) and 2 ml of THF were added to the amorphous solid, and the mixture was stirred in an atmosphere of argon at room temperature overnight.

This reaction mixture was concentrated. The residue was dissolved in water, washed with hexane and subjected to freeze-drying, whereby a crude ammonium sodium 3-(4-isopropyl-3,3-dimethyl-2,3-dihydrofuran-5-yl) phenylphosphate was obtained in the form of an amorphous solid in a yield of 542 mg.

$^1$HNMR (300 MHz, CD$_3$OD): δ1.14 (d, J=7.2 Hz, 6H), 1.25 (s, 6H), 2.79 (sept, J=7.2 Hz, 1H), 3.88 (s, 2H), 7.00–7.05 (m, 1H), 7.19–7.30 (m, 3H) ppm IR (KBr): 2964, 2872, 1600, 1582, 1224, 1108 cm$^{-1}$ Mass (FAB-pos, m/z, %): 379 ([M+Na−NH$_4$+Na]$^+$, 18), 357 ([M+H−NH$_4$+Na]$^+$, 100), 335 (29), 125 (25)

EXAMPLE 4

5-isopropyl-4,4-dimethyl-1-(3'-phosphoryloxy) phenyl-2,6,7-trioxabicyclo[3.2.0]heptane disodium salt (Compound [17])

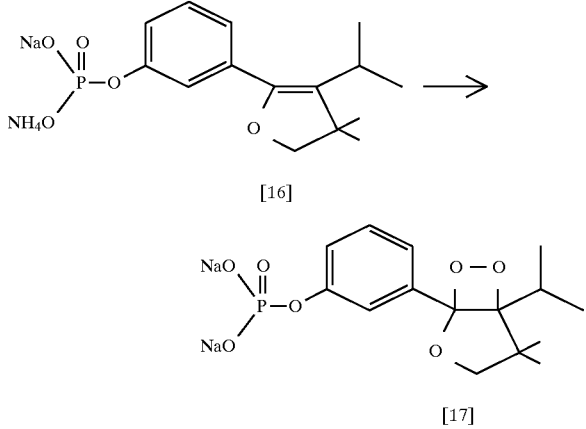

209 mg of the crude product of the compound [16] synthesized in Reference Example 12 and 2.5 mg of TPP were dissolved in a mixed solvent of 20 ml of dichloromethane and 4 ml of methanol. The solution was stirred in an atmosphere of oxygen at 0° C.

This solution was irradiated with a sodium lamp (180 w) for 2 hours.

The reaction mixture was then concentrated. The residue was dissolved in methanol and filtered through a 0.45μ polytetrafluoroethylene filter to remove insoluble components therefrom.

The filtrate was concentrated, and the residue was dissolved in a mixed solvent composed of 1.0 ml of methanol and 0.8 ml of a 0.1% aqueous solution of sodium hydrogencarbonate.

The above solution was subjected to HPLC using a polymeric reversed phase C18 column, and a fraction, which was eluted with a gradient elution by using a 0.1% aqueous solution of sodium hydrogencarbonate and acetonitrile, was subjected to freeze-drying, whereby a freeze-dried product was obtained.

The thus obtained freeze-dried product was dissolved in water and was then subjected to HPLC using a polymeric reversed phase C18 column, and a fraction, which was desalted with a gradient elution using water and acetonitrile, was subjected to freeze-drying, whereby 5-isopropyl-4,4-dimethyl-1-(3'-phosphoryloxy)phenyl-2,6,7-trioxabicyclo [3.2.0]heptane disodium salt (Compound [17]) was obtained in the form of an amorphous solid in a yield of 52 mg.

$^1$HNMR (300 MHz, CD$_3$OD): δ0.74 (d, J=7.0 Hz, 3H), 0.88 (d, J=7.0 Hz, 3H), 1.12 (s, 3H), 1.25 (s, 3H), 2.25 (sept, J=7.0 Hz, 1H), 3.83 (d, J=8.2 Hz, 1H), 4.44 (d, J=8.2 Hz, 1H), 7.06 (d with fine coupling, J=7.7 Hz, 1H), 7.22–7.31 (m, 2H), 7.57 (d with fine coupling, J=8.2 Hz, 1H) ppm IR (KBr): 2976, 1608, 1588, 1280, 1112 cm$^{-1}$ Mass (FAB-pos, m/z, %): 411 ([M+Na]$^+$, 80), 389 ([M+H]$^+$, 100), 367 (18), 115 (54)

Reference Example 13

(3-hydroxy-2,2,4,4-tetramethyl)pentyl 3-methoxybenzoate (Compound [18])

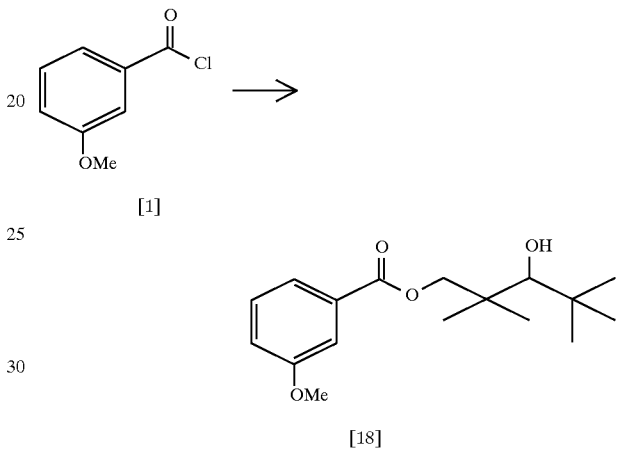

3.937 g (24.6 mmol) of 2,2,4,4-tetramethyl-1,3-pentanediol and 4.0 ml (49.5 mmol) of pyridine were dissolved in 10 ml of 1,2-dichloroethane, and the solution was stirred in an atmosphere of argon at 0° C.

To this solution, there was added dropwise over a period of 1 hour a solution of 3.70 ml (26.3 mmol) of m-anisoyl chloride in 40 ml of 1,2-dichloroethane, and the mixture was stirred at 0° C. with iced water cooling for 3 hours and 30 minutes.

This reaction mixture was poured into a saturated aqueous solution of sodium chloride. The mixture was then extracted with chloroform. The extract layer was washed with a saturated aqueous solution of sodium chloride, dried over magnesium sulfate, and then concentrated.

The residue was chromatographed on silica gel and eluted with a mixed solvent of chloroform and ethyl acetate (100:1), whereby (3-hydroxy-2,2,4,4-tetramethyl)pentyl 3-methoxybenzoate (Compound [18]) was obtained in the form of a colorless oil in a yield of 6.263 g (86.6%).

$^1$HNMR (300 MHz, CDCl$_3$): δ1.06 (s, 9H), 1.11 (s, 3H), 1.19 (s, 3H), 1.98–2.10 (m, 1H), 3.28 (d, J=4.4 Hz, 1H), 3.86 (s, 3H), 3.99 (d, J=10.8 Hz, 1H), 4.46 (d, J=10.8 Hz, 1H), 7.12 (ddd, J=8.2, 2.6 and 0.9 Hz, 1H), 7.37 (dd, J=8.2 and 7.7 Hz, 1H), 7.57 (dd, J=2.6 and 1.5 Hz, 1H), 7.63 (d with fine coupling, J=7.7 Hz, 1H) ppm IR (liq. film): 3556, 2964, 1716, 1602, 1588, 1470, 1372, 1280 cm$^{-1}$ Mass (m/z, %): 294 (M$^+$, 3), 237 (19), 153 (22), 152 (85), 135 (100), 107 (11)

Reference Example 14

(2,2,4,4-tetramethyl-3-oxo)pentyl 3-methoxybenzoate (Compound [19])

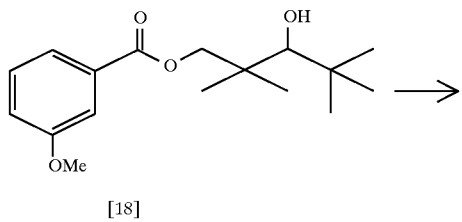

[18]

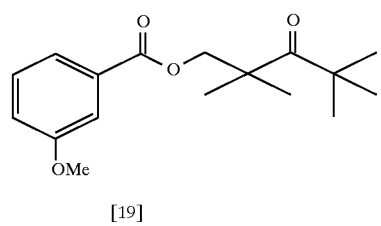

[19]

3.511 g (11.9 mmol) of the compound [18] synthesized in Reference Example 13 and 10.0 g of celite were added to 50 ml of dichloromethane. The mixture was stirred in an atmosphere of argon at room temperature.

To this mixture, 2.83 g (13.1 mmol) of pyridinium chlorochromate was added, and the mixture was stirred for 5 hours. To this mixture, 383 mg (1.78 mmol) of pyridinium chlorochromate was further added, and the mixture was stirred for 1 hour and 30 minutes.

To this reaction mixture, diethyl ether was added. The mixture was filtered through celite, and the filtrate was concentrated.

The residue was chromatographed on silica gel and eluted with a mixed solvent of hexane and ethyl acetate (5:1), whereby (2,2,4,4-tetramethyl-3-oxo)pentyl 3-methoxybenzoate (Compound [19]) was obtained in the form of a colorless oil in a yield of 2.947 g (84.5%).

$^1$HNMR (300 MHz, CDCl$_3$): δ1.28 (s, 9H), 1.38 (s, 6H), 3.83 (s, 3H), 4.40 (s, 2H), 7.09 (ddd, J=8.3, 2.7 and 1.0 Hz, 1H), 7.33 (dd, J=8.3 and 7.7 Hz, 1H), 7.50 (dd, J=2.5 and 1.5 Hz, 1H), 7.56 (d with fine coupling, J=7.7 Hz, 1H) ppm IR (liq. film): 2968, 1724, 1690, 1588, 1482, 1278, 1230 cm$^{-1}$ Mass (m/z, %): 292 (M$^+$, 2), 236 (32), 235 (22), 152 (42), 136 (14), 135 (100), 107 (14), 92 (11), 77 (11), 57 (28)

Reference Example 15

3-(3-methoxy)benzoyl-2,2,4,4-tetramethylpentanol (Compound [20])

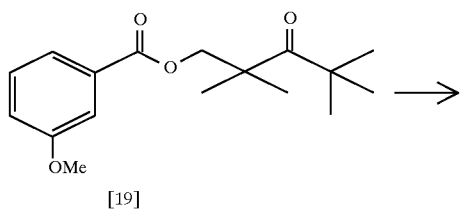

[19]

-continued

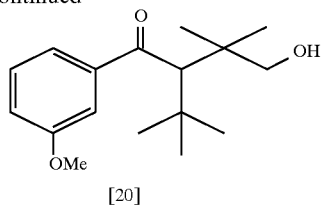

[20]

In an atmosphere of argon, 6.4 g (41.5 mmol) of titanium trichloride was suspended in 100 ml of anhydrous THF, and the suspension was stirred at room temperature for 25 minutes.

To this solution, 750 mg (19.8 mmol) of lithium aluminum hydride was added under ice cooling. The mixture was then stirred at room temperature for 30 minutes.

2.9 ml (20.8 mmol) of triethylamine was added to the above-mentioned mixture, and the mixture was refluxed for 1 hour and 10 minutes.

To this reaction mixture, there was added dropwise over a period of 50 minutes a solution of 1.23 g (4.21 mmol) of the compound [19] synthesized in Reference Example 14 in 20 ml of anhydrous THF, and the mixture was refluxed for 2 hours and 40 minutes.

This reaction mixture was poured into an aqueous solution of sodium hydrogencarbonate. The mixture was then extracted with ethyl acetate.

The ethyl acetate extract layer was successively washed with a saturated aqueous solution of sodium chloride and then with water, dried over magnesium sulfate, and then concentrated.

The residue was chromatographed on silica gel and eluted with a mixed solvent of hexane and ethyl acetate (5:1), whereby 3-(3-methoxy)benzoyl-2,2,4,4-tetramethylpentanol (Compound [20]) was obtained in the form of a colorless oil in a yield of 967 mg (82.6%).

IR (liq. film): 3448, 2960, 1676, 1596, 1584, 1488, 1260, 1048 cm$^{-1}$

Mass (m/z, %): 278 (M$^+$, 5), 260 (2), 206 (40), 191 (78), 152 (28), 135 (100), 107 (15), 83 (18)

Reference Example 16

4-t-butyl-5-(3-methoxy)phenyl-3,3-dimethyl-2,3-dihydrofuran (Compound [21])

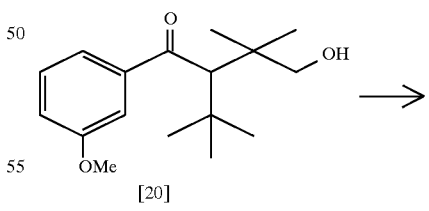

[20]

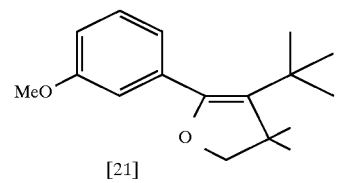

[21]

1.426 g (5.13 mmol) of the compound [20] synthesized in Reference Example 15 was dissolved in 20 ml of 1,2- dichloroethane, and the solution was stirred in an atmosphere of argon at room temperature.

To this solution, 130 mg (0.517 mmol) of pyridinium p-toluenesulfonate was added, and the mixture was stirred for 3 hours.

This reaction mixture was poured into an aqueous solution of sodium hydrogencarbonate. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (10:1), whereby 4-t-butyl-5-(3-methoxy)phenyl-3,3-dimethyl- 2,3-dihydrofuran (Compound [21]) was obtained in the form of a colorless oil in a yield of 1.155 g (86.6%).

$^1$HNMR (300 MHz, CDCl$_3$): δ1.06 (s, 9H), 1.33 (s, 6H), 3.81 (s, 3H), 3.87 (s, 2H), 6.81–6.92 (m, 3H), 7.20–7.28 (m, 1H) ppm IR (liq. film): 2960, 1596, 1484, 1316, 1052 cm$^{-1}$ Mass (m/z, %): 260 (M$^+$, 40), 246 (27), 245 (100), 189 (29), 135 (49), 107 (10), 57 (18)

EXAMPLE 5

5-t-butyl-1-(3-methoxy)phenyl-4,4-dimethyl-2,6,7-trioxabicyclo[3.2.0]heptane (Compound [22])

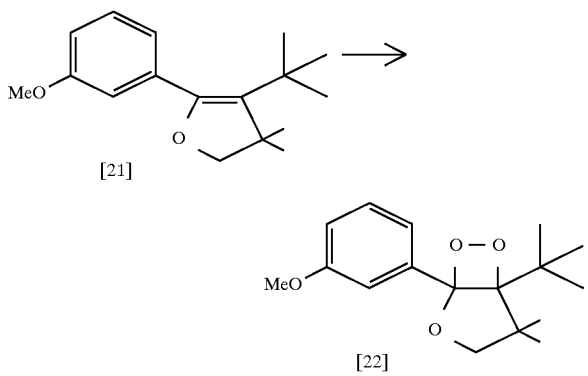

72 mg (0.277 mmol) of the compound [21] synthesized in Reference Example 16 and 2 mg of TPP were dissolved in 20 ml of dichloromethane, and the solution was stirred in an atmosphere of oxygen at −78° C.

This solution was irradiated with a sodium lamp (180 W) for 3 hours. The reaction mixture was then concentrated.

The residue was chromatographed on silica gel and eluted with a mixed solvent of hexane and dichloromethane (3:1 to 2:1), whereby 5-t-butyl-1-(3-methoxy)phenyl-4,4-dimethyl-2,6,7-trioxabicyclo[3.2.0]heptane (Compound [22]) was obtained in a yield of 71 mg (87.8%).

Melting Point: 92.5°–93.5° C. (grains, recrystallized from hexane and ethyl ether)

$^1$HNMR (300 MHz, CDCl$_3$): δ 1.00 (s, 9H), 1.15 (s, 3H), 1.37 (s, 3H), 3.81 (d, J=8.1 Hz, 1H), 3.83 (s, 3H), 4.58 (d, J=8.1 Hz, 1H), 6.93 (ddd, J=8.1, 2.5 and 1.2 Hz, 1H), 7.16–7.34 (m, 3H) ppm IR (KBr): 2972, 2896, 1612, 1584, 1222, 1034 cm$^{-1}$ Mass (m/z, %): 292 (M$^+$, 1), 260 (8), 245 (15), 236 (18), 235 (13), 152 (25), 135 (100)

Reference Example 17

4-t-butyl-5-(3-hydroxy)phenyl-3,3-dimethyl-2,3-dihydrofuran (Compound [23])

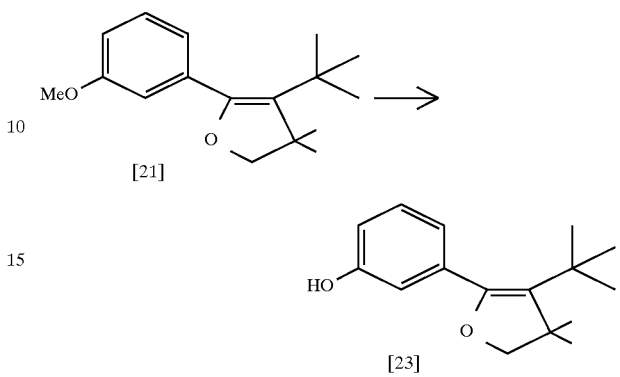

In an atmosphere of argon, 0.7 ml (9.45 mmol) of ethanethiol was added to a suspension prepared by dispersing 360 mg (9.00 mmol) of sodium hydride (60%) in 7.5 ml of anhydrous DMF, and the mixture was stirred for 20 minutes.

To the above solution, there was added a solution of 1.049 g (4.03 mmol) of the compound [21] synthesized in Reference Example 16 in 7.5 ml of anhydrous DMF, and the mixture was stirred at 150° C. for 2 hours and 30 minutes.

This reaction mixture was poured into a saturated aqueous solution of sodium chloride. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (6:1), whereby 4-t-butyl-5-(3-hydroxy)phenyl-3,3-dimethyl-2,3-dihydrofuran (Compound [23]) was obtained in a yield of 936 mg (94.3%).

Melting Point: 101.0°–101.5° C. (colorless needles, recrystallized from hexane and ethyl acetate)

$^1$HNMR (300 MHz, CDCl$_3$): δ1.06 ( s, 9H), 1.32 ( s, 6H), 3.86 (t, 2H), 4.69 (s, 1H), 6.75–6.81 (m, 2H), 6.88 (broad d, J=7.7 Hz, 1H), 7.16–7.23 (m, 1H) ppm IR (KBr): 3392, 2968, 1594, 1442, 1312, 1048 cm$^{-1}$ Mass (m/z, % ): 246 (M$^+$, 29), 232 (16), 231 (100), 175 (17), 121 (32)

Reference Example 18

4-t-butyl-5-(3-t-butyldimethylsiloxy)phenyl-3,3-dimethyl-2,3-dihydrofuran (Compound [24])

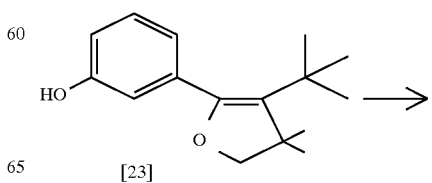

-continued

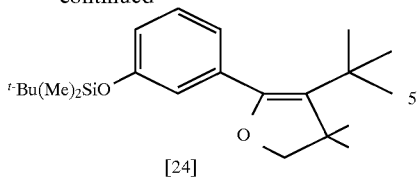

[24]

204 mg (0.829 mmol) of the compound [23] synthesized in Reference Example 17 was dissolved in 3 ml of anhydrous DMF, and the solution was stirred in an atmosphere of argon at room temperature.

To this solution, 122 mg (1.79 mmol) of imidazole and 236 mg (1.57 mmol) of t-butyldimethylchlorosilane were added, and the mixture was stirred for 4 hours.

This reaction mixture was poured into water. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (20:1), whereby 4-t-butyl-5-(3-t-butyldimethylsiloxy)phenyl-3,3-dimethyl-2,3-dihydrofuran (Compound [24]) was obtained in the form of a colorless oil in a yield of 296 mg (99.2%).

$^1$HNMR (300 MHz, CDCl$_3$): δ0.18 (s, 6H), 0.98 (s, 9H), 1.05 (s, 9H), 1.32 (s, 6H), 3.86 (s, 2H), 6.75–6.82 (m, 2H), 6.88 (d with fine coupling, J=7.5 Hz, 1H), 7.13–7.22 (m, 1H) ppm IR (liq. film): 2960, 1596, 1580, 1482, 1314, 1054 cm$^{-1}$ Mass (m/z, %): 361 (M$^+$+1, 11), 360 (M$^+$, 40), 346 (52), 345 (100), 289 (21), 231 (10), 57 (11)

EXAMPLE 6

5-t-butyl-1-(3-t-butyldimethylsiloxy)phenyl-4,4-dimethyl-2,6,7-trioxabicyclo[3.2.0]heptane (Compound [25])

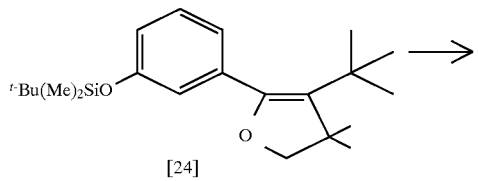

105 mg (0.292 mmol) of the compound [24] synthesized in Reference Example 18 and 2 mg of TPP were dissolved in 20 ml of dichloromethane, and the solution was stirred in an atmosphere of oxygen at −78° C.

This solution was irradiated with a sodium lamp (180 W) for 1 hour and 30 minutes. The reaction mixture was then concentrated.

The residue was chromatographed on silica gel and eluted with a mixed solvent of hexane and ethyl acetate (20:1), whereby 5-t-butyl-1-(3-t-butyldimethylsiloxy)phenyl-4,4-dimethyl-2,6,7-trioxabicyclo[3.2.0]heptane (Compound [25]) was obtained in the form of a colorless oil in a yield of 110 mg (96.2%).

$^1$HNMR (300 MHz, CDCl$_3$): δ0.18 (s, 6H), 0.98 (s, 9H), 1.00 (s, 9H), 1.15 (s, 3H), 1.36 (s, 3H), 3.80 (d, J=8.2 Hz, 1H), 4.47 (d, J=8.2 Hz, 1H), 6.86 (d with fine coupling, J=7.4 Hz, 1H), 7.11 (s with fine coupling, 1H), 7.18–7.29 (m, 1H) ppm IR (liq. film): 2964, 2936, 2896, 2864, 1604, 1588, 1256, 1032 cm$^{-1}$ Mass (m/z, %): 392 (M$^+$, 5), 360 (3), 336 (24), 335 (16), 279 (44), 235 (100), 195 (20)

Reference Example 19

3-(4-t-butyl-3,3-dimethyl-2,3-dihydrofuran-5-yl) phenylethylenephosphate (Compound [26])

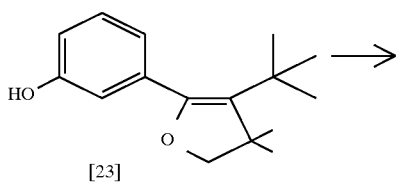

[23]

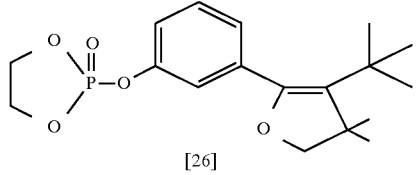

[26]

In an atmosphere of argon, 511 mg (2.08 mmol) of the compound [23] synthesized in Reference Example 17 was added to 7 ml of anhydrous toluene, and the mixture was stirred at 0° C.

To this solution, 0.35 ml (2.51 mmol) of triethylamine was added, and 0.2 ml (2.16 mmol) of 2-chloro-1,3,2-dioxaphosphoran-2-oxide was further added thereto. The mixture was stirred at 0° C. for 10 minutes and then at room temperature for 1 hour.

The reaction mixture was concentrated, and ether was added thereto.

Insoluble components were removed from the mixture by filtration. The filtrate was concentrated, whereby a crude 3-(4-t-butyl-3,3-dimethyl-2,3-dihydrofuran-5-yl) phenylethylenephosphate (Compound [26]) was obtained in the form of a colorless oil in a yield of 750 mg.

$^1$HNMR (300 MHz, CDCl$_3$): δ1.05 (s, 9H), 1.33 (s, 6H), 3.87 (s, 2H), 4.13–4.30 (m, 2H), 4.37–4.55 (m, 2H), 7.14–7.37 (m, 4H) ppm

Reference Example 20 sodium 3-(4-t-butyl-3,3-dimethyl-2,3-dihydrofuran-5-yl)phenyl-2'-cyanoethylphosphate (Compound [27])

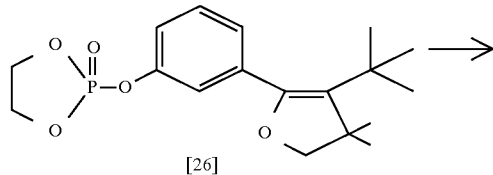

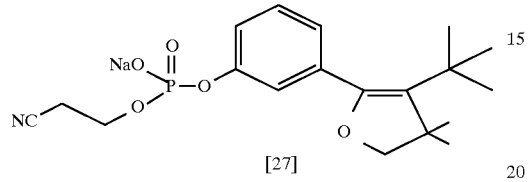

750 mg of the crude product of the compound [26] synthesized in Reference Example 19 was added to 10 ml of anhydrous DMF, and the mixture was stirred in an atmosphere of argon at room temperature.

To this solution, 116 mg (2.25 mmol) of sodium cyanide (95%) was added. The mixture was stirred overnight, and then concentrated.

The residue was dissolved in hexane, extracted with water and subjected to freeze-drying, whereby a crude sodium 3-(4-t-butyl-3,3-dimethyl-2,3-dihydrofuran-5-yl)phenyl-2'-cyanoethylphosphate (Compound [27]) was obtained in the form of an amorphous solid in a yield of 828 mg.

$^1$HNMR (300 MHz, CD$_3$OD): δ1.06 (s, 9H), 1.33 (s, 6H), 3.82 (s, 2H), 6.96 (d with fine coupling, J=6.6 Hz, 1H), 7.15 (s with fine coupling, 1H), 7.20–7.31 (m, 2H) ppm IR (KBr): 2960, 2256, 1600, 1580, 1248, 1108, 1052 cm$^{-1}$ Mass (FAB-pos, m/z, %): 424 ([M+Na]$^+$, 100), 402 ([M+H]$^+$, 22)

Reference Example 21 ammonium sodium 3-(4-t-butyl-3,3-dimethyl-2,3-dihydrofuran-5-yl)phenylphosphate (Compound [28])

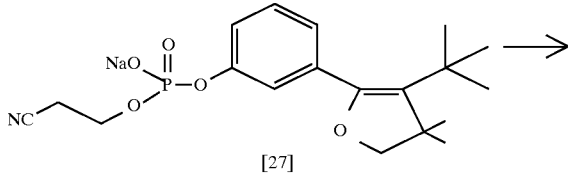

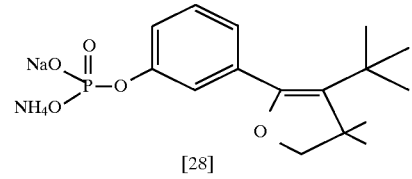

736 mg of the crude product of the compound [27] synthesized in Reference Example 20 was added to 7 ml of ammonia water (28%), and the mixture was stirred for 3 days.

This reaction mixture was concentrated. The residue was dissolved in hexane and extracted with water. The extract layer was subjected to freeze-drying, whereby a crude ammonium sodium 3-(4-t-butyl-3,3-dimethyl-2,3-dihydrofuran-5-yl)phenylphosphate was obtained in the form of an amorphous solid in a yield of 745 mg.

$^1$HNMR (300 MHz, CD$_3$OD): δ1.06 (s, 9H), 1.32 (s, 6H), 3.81 (s, 2H), 6.88–6.94 (m, 1H), 7.15 (broad s, 1H), 7.18–7.30 (m, 2H) ppm IR (KBr): 2960, 2868, 1598, 1580, 1212, 1052 cm$^{-1}$ Mass (FAB-pos, m/z, %):393 ([M+Na–NH$_4$+Na]$^+$, 14), 371 ([M+H–NH$_4$+Na]$^+$, 100), 349 (41), 125 (20)

EXAMPLE 7

5-t-butyl-4,4-dimethyl-1-(3'-phosphoryloxy)phenyl-2,6,7-trioxabicyclo[3.2.0]heptane disodium salt (Compound [29])

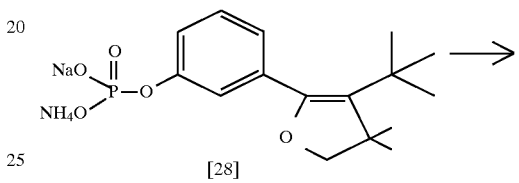

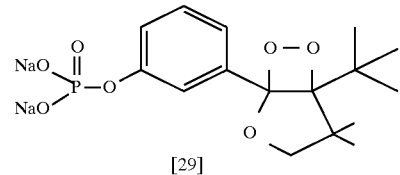

220 mg of the crude product of the compound [28] synthesized in Reference Example 21 and 3.5 mg of TPP were dissolved in a mixed solvent of 20 ml of dichloromethane and 5 ml of methanol.

This mixture was stirred in an atmosphere of argon at 0° C. for 2 hours. The solution was then irradiated with a sodium lamp (180 W) for 2 hours.

This reaction mixture was concentrated. Methanol was added to the residue. The mixture was filtered through a 0.45µ polytetrafluoroethylene filter to remove insoluble components therefrom.

The filtrate was concentrated, and the residue was dissolved in a mixed solvent composed of 1.0 ml of methanol and 0.8 ml of a 0.1% aqueous solution of sodium hydrogencarbonate.

The above solution was subjected to HPLC using a polymeric reversed phase C18 column, and a fraction, which was eluted with a gradient elution by using a 0.1% aqueous solution of sodium hydrogencarbonate and acetonitrile, was subjected to freeze-drying, whereby a freeze-dried product was obtained.

The thus obtained freeze-dried product was dissolved in water and the solution was subjected to HPLC using a polymeric reversed phase C18 column, and a fraction, which was desalted with a gradient elution using water and acetonitrile, was subjected to freeze-drying, whereby 5-t-butyl-4,4-dimethyl-1-(3'-phosphoryloxy)phenyl-2,6,7-trioxabicyclo[3.2.0]heptane disodium salt (Compound ([29]) was obtained in the form of an amorphous solid in a yield of 60 mg.

$^1$HNMR (300 MHz, CD$_3$OD): δ0.99 (s, 9H), 1.12 (s, 3H), 1.38 (s, 3H), 3.77 (d, J=8.0 Hz, 1H), 4.46 (d, J=8.0 Hz, 1H), 7.12 (d with fine coupling, J=7.9 Hz, 1H), 7.25 (dd, J=8.1 and 7.9 Hz, 1H), 7.30 (broad s, 1H), 7.61 (d with fine coupling, J=8.1 Hz, 1H) ppm IR(KBr): 2980, 1606, 1588, 1218, 1114 cm$^{-1}$ Mass (FAB-pos, m/z, %): 425 ([M+Na]$^+$, 54), 403 ([M+H]$^+$, 100), 381 (30), 115 (78)

Reference Example 22

5-(3-hydroxy)phenyl-3,3-dimethyl-4-phenyl-2,3-dihydrofuran (Compound [31])

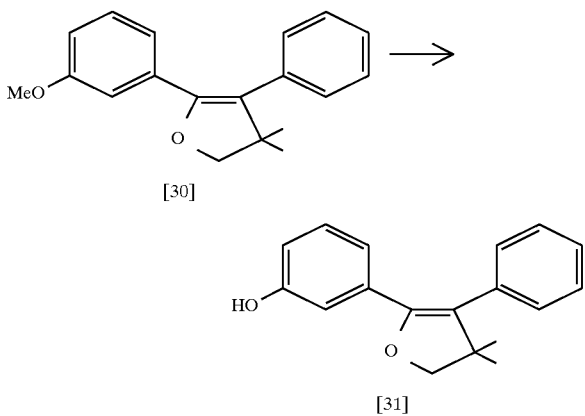

In an atmosphere of argon, 0.2 ml (2.70 mmol) of ethanethiol was added to a suspension prepared by dispersing 91 mg (2.28 mmol) of sodium hydride (60%) in 3 ml of anhydrous DMF, and the mixture was stirred at room temperature for 20 minutes.

To this solution, there was added a solution of 282 mg (1.01 mmol) of 4-phenyl-5-(3-methoxy)phenyl-3,3-dimethyl-2,3-dihydrofuran in 2 ml of anhydrous DMF, and the mixture was stirred at 130° C. for 3 hours.

This reaction mixture was poured into a saturated aqueous solution of sodium chloride. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (10:1), whereby 5-(3-hydroxy)phenyl-3,3-dimethyl-4-phenyl- 2,3-dihydrofuran (Compound [31]) was obtained in a yield of 215 mg (80.3%).

Melting Point: 114°–115° C. (colorless powdery crystals, recrystallized from hexane)

$^1$HNMR (300 MHz, CDCl$_3$): δ1.19 (s, 6H), 4.20 (s, 2H), 4.49 (s, 1H), 6.66 (ddd, J=7.9, 2.6 and 1.0 Hz, 1H), 6.74–6.78 (m, 1H), 6.81 (d with fine coupling, J=7.9 Hz, 1H), 7.01 (t, J=7.9 Hz, 1H), 7.17–7.23 (m, 2H), 7.30–7.39 (m, 3H) ppm IR (liq. film): 3260, 2964, 1580, 1464, 1366, 1230, 1088 cm$^{-1}$ Mass (m/z, %): 266 (M$^+$, 54), 252 (19), 251 (100), 121 (17)

Reference Example 23

5- (3-t-butyldimethylsiloxy)phenyl-3,3-dimethyl-4-phenyl-2,3-dihydrofuran (Compound [32])

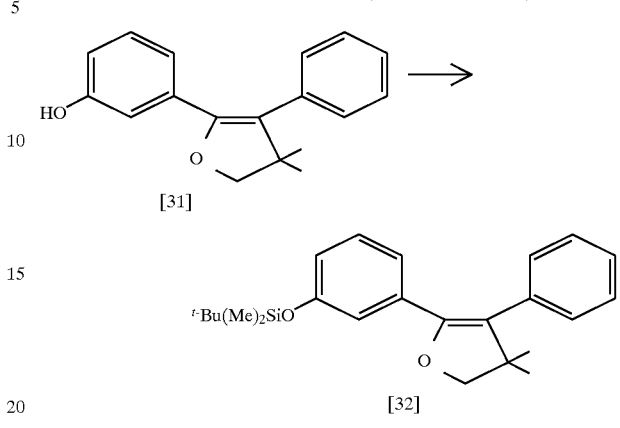

160 mg (0.602 mmol) of the compound [31] synthesized in Reference Example 22 was dissolved in 3 ml of anhydrous DMF, and the solution was stirred in an atmosphere of argon at room temperature.

To this solution, 90 mg (1.32 mmol) of imidazole and 60 mg (1.06 mmol) of t-butyldimethylchlorosilane were added, and the mixture was stirred overnight.

This reaction mixture was poured into water. The mixture was then extracted with ethyl acetate.

The ethyl acetate extract layer was successively washed with a saturated aqueous solution of sodium chloride, and then with water, dried over magnesium sulfate, and then concentrated.

The residue was chromatographed on silica gel and eluted with a mixed solvent of hexane and ethyl acetate (10:1), whereby 5-(3-t-butyldimethylsiloxy)phenyl-3,3-dimethyl-4-phenyl-2,3-dihydrofuran (Compound [32]) was obtained in the form of a colorless oil in a yield of 217 mg (94.9%).

$^1$HNMR (300 MHz, CDCl$_3$): δ0.01 (s, 6H), 0.90 (s, 9H), 1.19 (s, 6H), 4.21 (s, 2H), 6.66 (ddd, J=7.9, 2.4 and 1.1 Hz, 1H), 6.70–6.73 (m, 1H), 6.96 (d with fine coupling, J=7.9 Hz, 1H), 7.05 (t, J=7.9 Hz, 1H), 7.18–7.24 (m, 2H), 7.28–7.39 (m, 3H) ppm IR (liq. film): 2932, 1600, 1578, 1440, 1276 cm$^{-1}$ Mass (m/z, %): 380 (M$^+$, 47), 366 (30), 365 (100)

EXAMPLE 8

1-(3-t-butyldimethylsiloxy)phenyl-4,4-dimethyl-5-phenyl-2,6,7-trioxabicyclo[3.2.0]heptane (Compound [33])

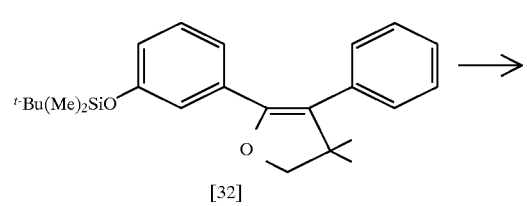

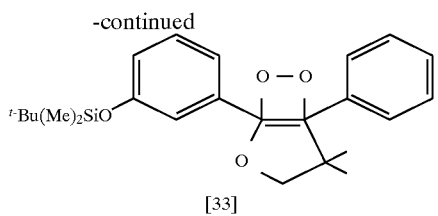

[33]

102 mg (0.268 mmol) of the compound [32] synthesized in Reference Example 23 and 2 mg of TPP were dissolved in 20 ml of dichloromethane, and the solution was stirred in an atmosphere of oxygen at −78° C.

This solution was irradiated with a sodium lamp (180 W) for 3 hours. The reaction mixture was then concentrated.

The residue was chromatographed on silica gel and eluted with a mixed solvent of hexane and ether (20:1), whereby 1-(3-t-butyldimethylsiloxy)phenyl-4,4-dimethyl-5-phenyl-2,6,7-trioxabicyclo[3.2.0]heptane (Compound [33]) was obtained in the form of an amorphous solid in a yield of 77 mg (69.6%).

$^1$HNMR (300 MHz, CDCl$_3$): δ0.05 (s, 6H), 0.85 (s, 3H), 0.92 (s, 9H), 1.02 (s, 3H), 4.22 (d, J=8.2 Hz, 1H), 4.86 (d, J=8.2 Hz, 1H), 6.65–6.72 (m, 2H), 6.82–6.88 (m, 1H), 7.05–7.09 (m, 1H), 7.11–7.22 (m, 5H) ppm IR (liq. film): 2956, 2932, 2896, 2860, 1606, 1590, 1490, 1230, 1012 cm$^{-1}$ Mass (m/z, %): 412 (M$^+$, 14), 356 (20), 355 (26), 326 (25), 325 (100), 300 (20), 299 (49), 256 (11), 255 (55), 235 (36), 179 (28), 151 (12), 150 (17), 135 (19), 105 (49)

Reference Example 24

(3-hydroxy-1-t-butyl-2,2,4,4-tetramethyl)pentyl 3-methoxybenzoate (Compound [34])

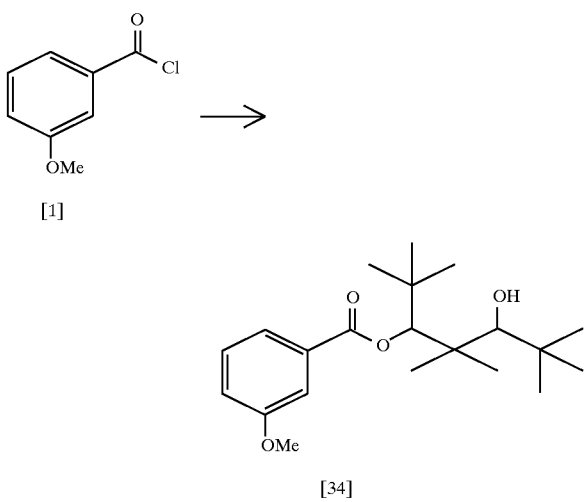

1.14 g (5.69 mmol) of 2,2,4,4,6,6-hexamethyl-3,5-heptanediol and 1.0 mmol) of pyridine were dissolved in 15 ml of 1,2-dichloroethane. The solution was stirred in an atmosphere of nitrogen at 0° C.

To this solution, 0.80 ml (5.69 mmol) of m-anisoyl chloride (Compound [1]) was added, and the mixture was then stirred at room temperature overnight.

This reaction mixture was poured into a saturated aqueous solution of sodium chloride. The mixture was then extracted with ethyl acetate. The ethyl acetate extract layer was washed with a saturated aqueous solution of sodium chloride three times, dried over magnesium sulfate, and concentrated.

The residue was crystallized from a mixed solvent of hexane and ethyl acetate, and the crystals were separated by filtration, whereby (3-hydroxy-1-t-butyl-2,2,4,4-tetramethyl)pentyl 3-methoxybenzoate (Compound [34]) was obtained in the form of colorless grains in a yield of 264 mg (14.3%).

The filtrate was concentrated, and the residue was chromatographed on silica gel and eluted with a mixed solvent of hexane and ethyl acetate (4:1), whereby the Compound [34] was further obtained in a yield of 1.26 g (68.5%).

Melting Point: 89.0°–89.5° C. (colorless grains, recrystallized from a mixed solvent of hexane and ethyl acetate)

$^1$HNMR(400 MHz, CDCl$_3$): δ1.03 (s, 9H), 1.14 (s, 9H), 1.16 (s, 3H), 1.28 (s, 3H), 2.98 (d, J=3.9 Hz, 1H), 3.36 (d, J=3.9 Hz, 1H), 3.87 (s, 3H), 5.11 (s, 1H), 7.13 (ddd, J=8.3, 2.4 and 1.0 Hz, 1H), 7.38 (dd, J=8.3 and 7.8 Hz, 1H), 7.59 (s with fine coupling, 1H), 7.65 (d with fine coupling, J=7.8 Hz, 1H)ppm Reference Example 25

(1-t-butyl-2,2,4,4-tetramethyl-3-oxo)pentyl 3-methoxybenzoate (Compound [35])

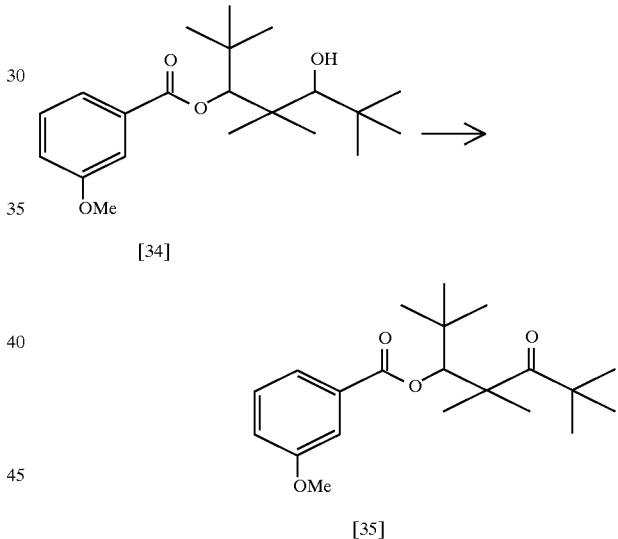

1.37 g (3.92 mmol) of the compound [34] synthesized in Reference Example 24 and 2.8 g of celite were added to 25 ml of dichloromethane. The mixture was stirred in an atmosphere of nitrogen at room temperature.

To this mixture, 903 mg (4.19 mmol) of pyridinium chlorochromate was added, and the mixture was stirred for 7.7 hours. To this mixture, 305 mg (1.41 mmol) of pyridinium chlorochromate was further added, and the mixture was stirred for 48 hours.

To this reaction mixture, diethyl ether was added. The mixture was filtered through celite, and the filtrate was concentrated.

The residue was chromatographed on silica gel and eluted with a mixed solvent of hexane and dichloromethane (2:1) and then with dichloromethane, whereby (1-t-butyl-2,2,4,4-tetramethyl-3-oxo)pentyl 3-methoxybenzoate (Compound [35]) was obtained in the form of a colorless oil in a yield of 1.34 g (98.5%).

$^1$HNMR(400 MHz, CDCl$_3$): δ0.98 (s, 9H), 1.18 (s, 3H), 1.35 (s, 9H), 1.46 (s, 3H), 3.87 (s, 3H), 5.94 (s, 1H), 7.13 (ddd, J=8.3, 3.0 and 1.0 Hz, 1H), 7.38 (dd, J=8.3 and 7.8 Hz, 1H), 7.63 (dd, J=3.0 and 1.5 Hz, 1H), 7.70 (d with fine coupling, J=7.8 Hz, 1H)ppm Reference Example 26

2,4-di-t-butyl-5-(3-methoxyphenyl)-3,3-dimethyl-2,3-dihydrofuran (Compound [36])

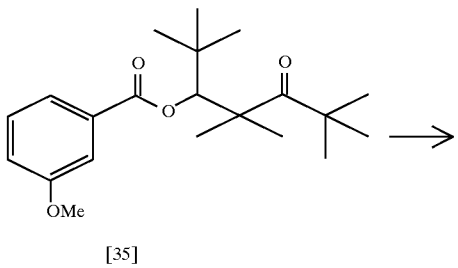

[35]

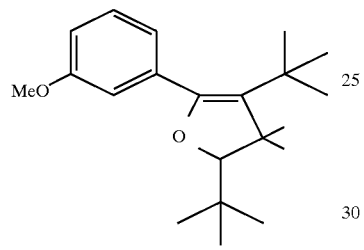

[36]

In an atmosphere of nitrogen, 5.82 g (37.7 mmol) of titanium trichloride was suspended in 100 ml of anhydrous THF, and the suspension was stirred at room temperature for 30 minutes.

To this solution, 820 mg (21.6 mmol) of lithium aluminum hydride was added, and the mixture was stirred at room temperature for 30 minutes.

3.0 ml (21.5 mmol) of triethylamine was added to the above-mentioned mixture, and the mixture was refluxed for 1 hour.

To this reaction mixture, there was added dropwise over a period of 10 minutes a solution of 1.28 g (6.68 mmol) of the compound [35] synthesized in Reference Example 25 in 20 ml of anhydrous THF, and the mixture was stirred for 50 minutes.

This reaction mixture was poured into an aqueous solution of sodium hydrogencarbonate. The mixture was then extracted with ethyl acetate.

The ethyl acetate extract layer was washed with a saturated aqueous solution of sodium chloride three times, dried over magnesium sulfate, and then concentrated.

The residue was chromatographed on silica gel and eluted with hexane, whereby 2,4-di-t-butyl-5-(3-methoxyphenyl)-3,3-dimethyl-2,3-dihydrofuran (Compound [36]) was obtained in the form of a colorless oil in a yield of 1.03 g (88.0%).

$^1$HNMR(400 MHz, CDCl$_3$): δ1.04 (s, 9H), 1.08 (s, 9H), 1.36 (s, 3H), 1.41 (s, 3H), 3.62 (s, 1H), 3.81 (s, 3H), 6.82–6.91 (m, 3H), 7.21–7.26 (m, 1H) ppm

EXAMPLE 9

3,5-di-t-butyl-4,4-dimethyl-1-(3-methoxyphenyl)-2,6,7-trioxabicyclo[3.2.0]heptane (Compound [37])

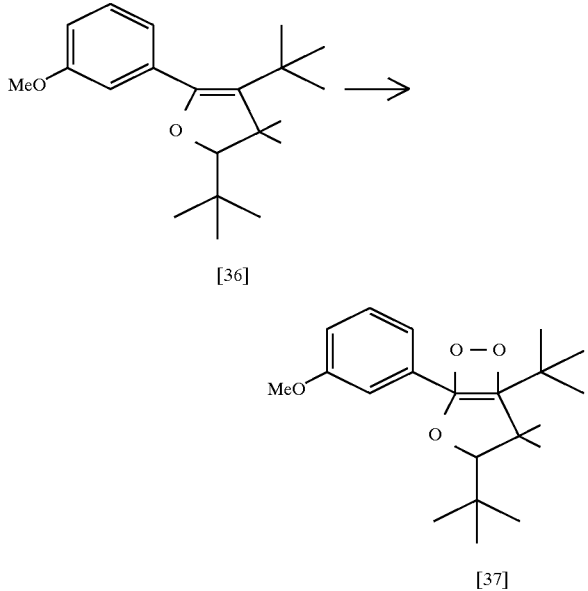

102 mg (0.323 mmol) of the compound [36] synthesized in Reference Example 26 and 1 mg of TPP were dissolved in 20 ml of dichloromethane, and the solution was stirred in an atmosphere of oxygen at 0° C.

This solution was irradiated with a sodium lamp (940 W) for 1 hour. The reaction mixture was then concentrated.

The residue was chromatographed on silica gel and eluted with hexane, whereby 3,5-di-t-butyl-4,4-dimethyl-1-(3-methoxyphenyl)-2,6,7-trioxabicyclo[3.2.0]heptane (Compound [37]) was obtained in a yield of 105 mg (93.5%).

Melting Point: 132.0°–134.0° C. (colorless grains, recrystallized from hexane)

$^1$HNMR(400 MHz, CDCl$_3$): δ1.02 (s, 9H), 1.19 (s, 9H), 1.25 (s, 3H), 1.31 (s, 3H), 3.82 (s, 3H), 4.42 (s, 1H), 6.92 (ddd, J=8.3, 2.4 and 1.0 Hz, 1H), 7.16–7.23 (m, 2H), 7.30 (dd, J=8.3 and 7.3 Hz, 1H) ppm Reference Example 27

2,4-di-t-butyl-5-(3-hydroxyphenyl)-3,3-dimethyl-2,3-dihydrofuran (Compound [38])

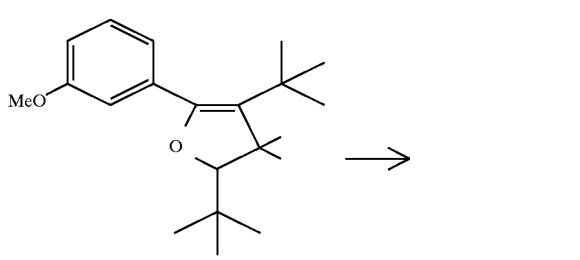

[36]

-continued

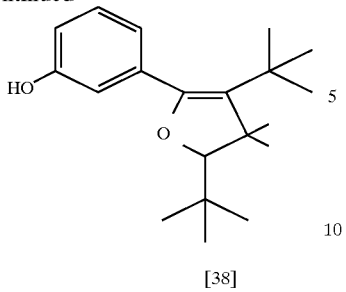

[38]

In an atmosphere of nitrogen, 128 mg (3.20 mol) of sodium hydride (60%) was dispersed in 4 ml of anhydrous DMF, and the mixture was stirred at room temperature to prepare a solution.

To this solution, 0.25 ml (3.38 mmol) of ethanethiol was added, and the mixture was stirred for 10 minutes.

To this solution, there was added a solution of 505 mg (1.60 mmol) of the compound [36] synthesized in Reference Example 26 in 4 ml of anhydrous DMF, and the mixture was refluxed for 1 hour.

This reaction mixture was poured into a saturated aqueous solution of sodium chloride. The mixture was then extracted with ethyl acetate.

The ethyl acetate extract layer was washed with a saturated aqueous solution of sodium chloride three times, dried over magnesium sulfate, and then concentrated.

The residue was chromatographed on silica gel and eluted with a mixed solvent of hexane and ethyl acetate (10:1 to 5:1), whereby 2,4-di-t-butyl-5-(3-hydroxyphenyl)-3,3-dimethyl-2,3-dihydrofuran (Compound [38]) was obtained in a yield of 474 mg (98.2%).

Melting Point: 97.0°–97.5° C. (colorless needles, recrystallized from hexane)

$^1$HNMR(400 MHz, CDCl$_3$): δ1.04 (s, 9H), 1.08 (s, 9H), 1.36 (s, 3H), 1.40 (s, 3H), 3.61 (s, 1H), 4.84 (s, 1H), 6.75–6.79 (m, 2H), 6.87 (d with fine coupling, J=7.8 Hz, 1H), 7.18 (dd, J=8.8 and 7.8 Hz, 1H)ppm Reference Example 28

2,4-di-t-butyl-5-[3-(t-butyldimethylsiloxy)phenyl]-3,3-dimethyl-2,3-dihydrofuran (Compound [39])

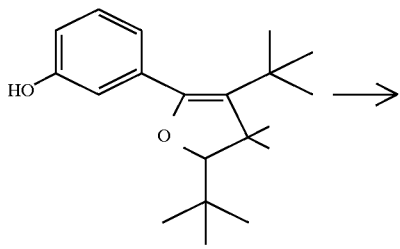

[38]

-continued

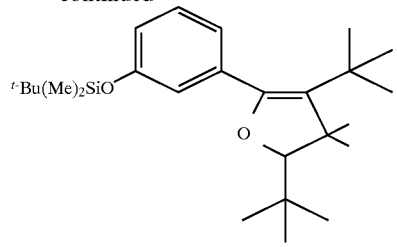

[39]

251 mg (0.803 mmol) of the compound [38] synthesized in Reference Example 27 was dissolved in 5 ml of anhydrous DMF, and the solution was stirred in an atmosphere of nitrogen at room temperature.

To this solution, 138 mg (2.03 mmol) of imidazole and 225 mg (1.49 mmol) of t-butyldimethylchlorosilane were added, and the mixture was stirred for 2 hours.

This reaction mixture was poured into a saturated aqueous solution of sodium chloride. The mixture was then extracted with ethyl acetate.

The ethyl acetate extract layer was washed with a saturated aqueous solution of sodium chloride two times, dried over magnesium sulfate, and then concentrated.

The residue was chromatographed on silica gel and eluted with hexane, whereby 2,4-di-t-butyl-5-[3-(t-butyldimethylsiloxy)phenyl]-3,3-dimethyl-2,3-dihydrofuran (Compound [39]) was obtained in the form of a colorless oil in a yield of 326 mg (94.3%).

$^1$HNMR(400 MHz, CDCl$_3$): δ0.19 (s, 6H), 0.98 (s, 9H), 1.03 (s, 9H), 1.07 (s, 9H), 1.36 (s, 3H), 1.40 (s, 3H), 3.61 (s, 1H), 6.75–6.80 (m, 2H), 6.88 (d with fine coupling, J=7.4 Hz, 1H), 7.13–7.19 (m, 1H)ppm

EXAMPLE 10

3,5-di-t-butyl-1-[3-(t-butyldimethylsiloxy)phenyl]-4,4-dimethyl-2,6,7-trioxabicyclo[3.2.0]heptane (Compound [40])

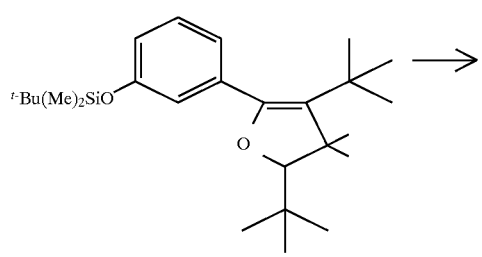

[39]

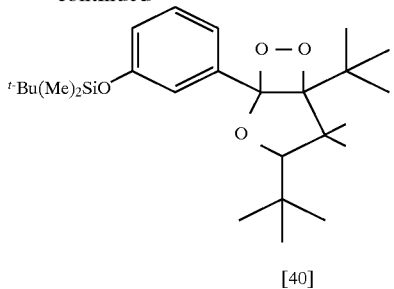

[40]

58 mg (0.139 mmol) of the compound [39] synthesized in Reference Example 28 and 1.5 mg of TPP were dissolved in 15 ml of dichloromethane, and the solution was stirred in an atmosphere of oxygen at 0° C.

This solution was irradiated with a sodium lamp (940 W) for 1 hour. The reaction mixture was then concentrated.

The residue was chromatographed on silica gel and eluted with hexane, whereby 3,5-di-t-butyl-1-[3-(t-butyldimethylsiloxy)phenyl]-4,4-dimethyl-2,6,7-trioxabicyclo[3.2.0]heptane (Compound [40]) was obtained in the form of a colorless oil in a yield of 59 mg (94.5%).

$^1$HNMR(400 MHz, CDCl$_3$): δ0.19 (s, 6H), 0.98 (s, 9H), 1.02 (s, 9H), 1.19 (s, 9H), 1.24 (s, 3H), 1.30 (s, 3H), 4.41 (s, 1H), 6.82–6.89 (m, 1H), 7.09 (broad s, 1H), 7.20–7.26 (m, 2H)ppm Reference Example 29

(3-hydroxy-2,2,4,4-tetramethyl-1-phenyl)pentyl 3-methoxybenzoate (Compound [41])

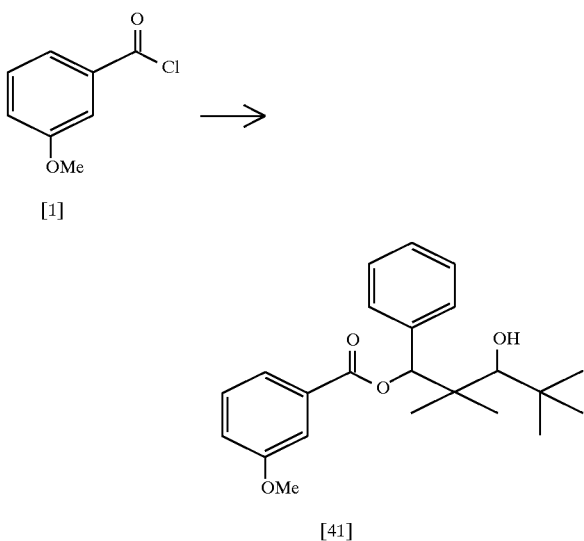

[1]

[41]

1.07 g (4.53 mmol) of 2,2,4,4-tetramethyl-1-phenyl-1,3-pentanediol and 0.73 ml (9.04 mmol) of pyridine were dissolved in a mixed solvent of 6 ml of dichloromethane and 3 ml of diethyl ether. The solution was stirred in an atmosphere of nitrogen at room temperature.

To this solution, 0.76 ml (5.40 mmol) of m-anisoyl chloride (Compound [1]) was added, and the mixture was then stirred at room temperature overnight.

This reaction mixture was poured into a saturated aqueous solution of sodium chloride. The mixture was then extracted with ethyl acetate. The ethyl acetate extract layer was washed with a saturated aqueous solution of sodium chloride, dried over magnesium sulfate, and concentrated.

The residue was crystallized from a mixed solvent of hexane and diethyl ether, whereby (3-hydroxy-2,2,4,4-tetramethyl-1-phenyl)pentyl 3-methoxybenzoate (Compound ([41]) was obtained in the form of a colorless needles in a yield of 1.38 g (82.2%).

$^1$HNMR(400 MHz, CDCl$_3$): δ1.00 (s, 9H), 1.16 (s, 3H), 1.23 (s, 3H), 1.62 (d, J=6.0 Hz, 1H), 3.14 (d, J=6.0 Hz, 1H), 3.85 (s, 3H), 6.16 (s, 1H), 7.11 (dd, J=8.0 and 2.6 Hz, 1H), 7.26–7.32 (m, 3H), 7.37 (t, J=8.0 Hz, 1H), 7.45 (d, J=6.4 Hz, 2H), 7.60 (s with fine coupling, 1H), 7.70 (d, J=7.0 Hz 1H)ppm Reference Example 30

(2,2,4,4-tetramethyl-3-oxo-1-phenyl)pentyl 3-methoxybenzoate (Compound [42])

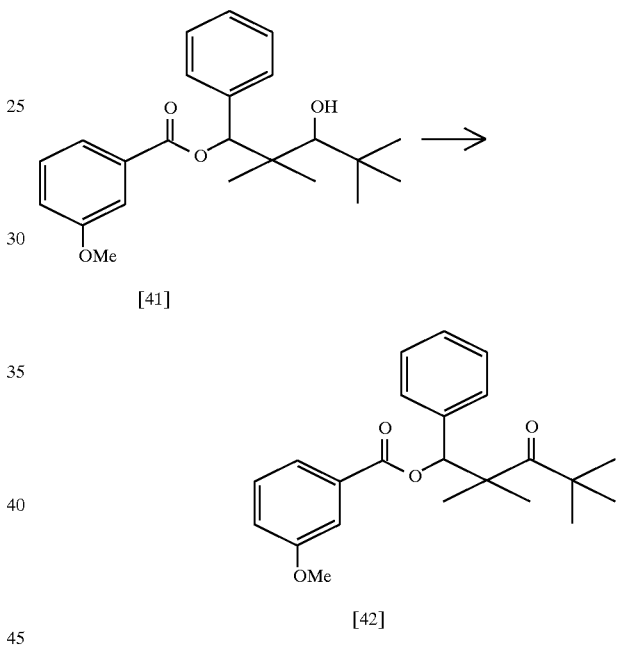

[41]

[42]

1.30 g (3.51 mmol) of the compound [41] synthesized in Reference Example 29 and 5.32 g of celite were added to 27 ml of dichloromethane. The mixture was stirred in an atmosphere of nitrogen at 0° C.

To this mixture, 0.742 g (3.44 mmol) of pyridinium chlorochromate was added, and the mixture was stirred overnight.

To this reaction mixture, diethyl ether was added. The mixture was filtered through celite, and the filtrate was concentrated.

The residue was chromatographed on silica gel and eluted with a mixed solvent of hexane and ethyl acetate (10:1), whereby (2,2,4,4-tetramethyl-3-oxo-1-phenyl)pentyl 3-methoxybenzoate (Compound [42]) was obtained in the form of a colorless oil in a yield of 1.12 g (86.7%).

$^1$HNMR(400 MHz, CDCl$_3$): δ1.19 (s, 9H), 1.27 (s, 3H), 1.44 (s, 3H), 3.84 (s, 3H), 6.51 (s, 1H), 7.10 (dd, J=8.2 and 2.3 Hz, 1H), 7.26–7.31 (m, 5H), 7.35 (t, J=8.2 Hz, 1H), 7.56 (t, J=2.3 Hz, 1H), 7.56 (d, J=7.8 Hz, 1H)ppm

Reference Example 31

4-t-butyl-5-(3-methoxyphenyl)-3,3-dimethyl-2-phenyl-2,3-dihydrofuran (Compound [43])

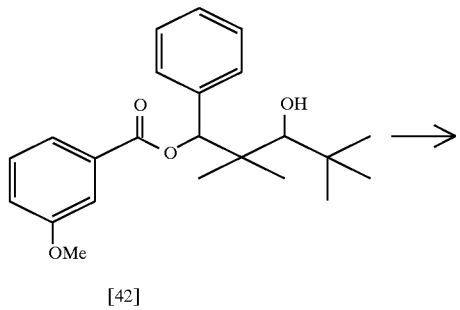

[42]

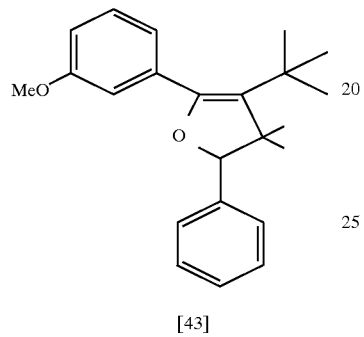

[43]

In an atmosphere of nitrogen, 4.65 g (30.1 mmol) of titanium trichloride was suspended in 100 ml of anhydrous THF, and the suspension was stirred at 0° C. for 30 minutes.

To this solution, 572 mg (15.1 mmol) of lithium aluminum hydride was added, and the mixture was stirred at room temperature for 1 hour.

2.1 ml (15 mmol) of triethylamine was added to the above-mentioned mixture, and the mixture was stirred for 1 hour.

To this solution, there was added dropwise over a period of 1 hour and 30 minutes a solution of 1.12 g (2.71 mmol) of the compound [42] synthesized in Reference Example 30 in 20 ml of anhydrous THF, and the mixture was refluxed for 2 hours.

This reaction mixture was poured into a saturated aqueous solution of sodium chloride. The mixture was then extracted with ethyl acetate.

The ethyl acetate extract layer was washed with a saturated aqueous solution of sodium chloride, dried over magnesium sulfate, and then concentrated.

The residue was crystallized from hexane, whereby 4-t-butyl-5-(3-methoxyphenyl)-3,3-dimethyl-2-phenyl-2,3-dihydrofuran (Compound [43]) was obtained in a yield of 717 mg (70.1%).

Melting Point: 79.0°–80.0° C. (colorless grains, recrystallized from hexane)

$^1$HNMR(400 MHz, CDCl$_3$): δ0.85 (s, 3H), 1.10 (s, 9H), 1.41 (s, 3H), 3.83 (s, 3H), 4.98 (s, 1H), 6.86–6.99 (m, 3H), 7.25–7.40 (m, 6H)ppm

EXAMPLE 11

5-t-butyl-1-(3-methoxyphenyl)-4,4-dimethyl-3-phenyl-2,6,7-trioxabicyclo[3.2.0]heptane (Compound [44])

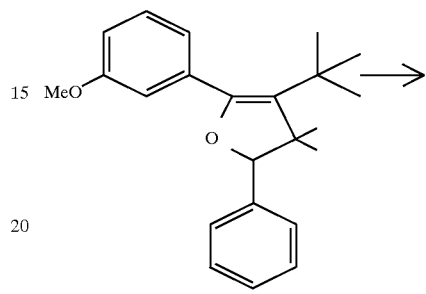

[43]

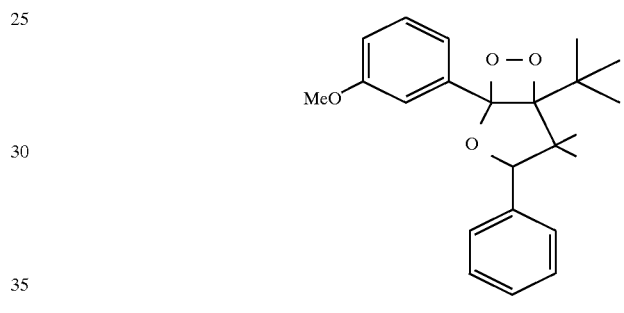

[44]

90.7 mg (0.270 mmol) of the compound [43] synthesized in Reference Example 31 and 0.5 mg of Rose Bengale were dissolved in 2.0 ml of acetone, and the solution was stirred in an atmosphere of oxygen at 0° C.

This solution was irradiated with a sodium lamp (940 W) for 2 hours. The reaction mixture was then concentrated.

The residue was subjected to preparative TLC and eluted with a mixed solvent of hexane and ethyl acetate (10:1), whereby 5-t-butyl-(3-methoxyphenyl)-4,4-dimethyl-3-phenyl-2,6,7-trioxabicyclo[3.2.0]heptane (Compound [44]) was obtained in the form of a colorless oil in a yield of 65.5 mg (65.6%).

$^1$HNMR(400 MHz, CDCl$_3$): δ0.88 (s, 3H), 1.06 (s, 9H), 1.20 (s, 3H), 3.86 (s, 3H), 5.76 (s, 1H), 6.95–6.97 (m, 1H), 7.25–7.40 (m, 8H)ppm

Reference Example 32

4-t-butyl-5-(3-hydroxyphenyl)-3,3-dimethyl-2-phenyl-2,3-dihydrofuran (Compound [45])

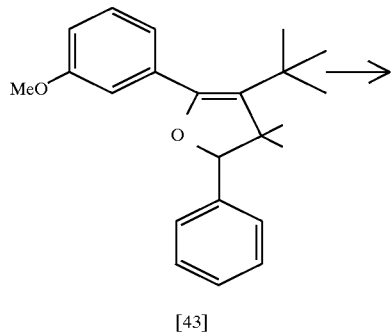

In an atmosphere of nitrogen, 120 mg (3.00 mmol) of sodium hydride (60%) was dispersed in 5 ml of anhydrous DMF, and the mixture was stirred at 0° C. to prepare a solution.

To this solution, 0.26 ml (3.51 mmol) of ethanethiol was added, and the mixture was stirred for 10 minutes.

To this solution, there was added 500 mg (1.49 mmol) of the compound [43] synthesized in Reference Example 31, and the mixture was refluxed for 2 hours and 30 minutes.

This reaction mixture was poured into a saturated aqueous solution of sodium chloride. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (5:1), whereby 4-t-butyl-5-(3-hydroxyphenyl)-3,3-dimethyl-2-phenyl-2,3-dihydrofuran (Compound [45]) was obtained in a yield of 448 mg (93.3%).

Melting Point: 93.0°–94.0° C. (colorless needles, recrystallized from hexane)

$^1$HNMR(400 MHz, CDCl$_3$): δ0.84 (s, 3H), 1.10 (s, 9H), 1.41 (s, 3H), 4.69 (s, 1H), 4.97 (s, 1H), 6.80 (dd, J=8.3 and 2.4 Hz, 1H), 6.86–6.87 (m, 1H), 6.97 (d, J=7.3 Hz, 1H), 7.22 (t, J=7.8 Hz, 1H), 7.28–7.39 (m, 5H)ppm

Reference Example 33

4-t-butyl-5-[3-(t-butyldimethylsiloxy)phenyl]-3,3-dimethyl-2-phenyl-2,3-dihydrofuran (Compound [46])

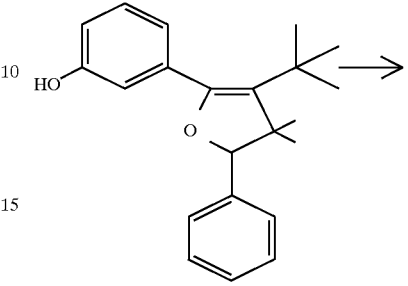

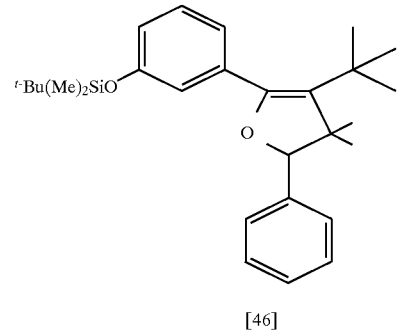

257 mg (0.797 mmol) of the compound [45] synthesized in Reference Example 32 was dissolved in 2 ml of anhydrous DMF, and the solution was stirred in an atmosphere of nitrogen at 0° C.

To this solution, 110 mg (1.60 mmol) of imidazole was added, and the mixture was stirred for 30 minutes.

To this reaction mixture, 216 mg (1.43 mmol) of t-butyldimethylchlorosilane were added, and the mixture was stirred for 1 hour and 30 minutes.

This reaction mixture was poured into a saturated aqueous solution of sodium chloride. The mixture was then extracted with ethyl acetate.

The ethyl acetate extract layer was washed with a saturated aqueous solution of sodium chloride, dried over magnesium sulfate, and then concentrated.

The residue was chromatographed on silica gel and eluted with a mixed solvent of hexane and ethyl acetate (7:1), whereby 4-t-butyl-5-[3-(t-butyldimethylsiloxy)-phenyl]-3,3-dimethyl-2-phenyl-2,3-dihydrofuran (Compound [46]) was obtained in the form of a colorless oil in a yield of 294 mg (84.6%).

$^1$HNMR(400 MHz, CDCl$_3$): δ0.20 (s, 6H), 0.84 (s, 3H), 0.99 (s, 9H), 1.09 (s, 9H), 1.41 (s, 3H), 4.98 (s, 1H), 6.79–6.86 (m, 2H), 6.96–6.99 (m, 1H), 7.20 (t, J=7.8 Hz, 1H), 7.28–7.40 (m, 5H)ppm

EXAMPLE 12

5-t-butyl-1-[3-(t-butyldimethylsiloxy)phenyl]-4,4-dimethyl-3-phenyl-2,6,7-trioxabicyclo[3.2.0]heptane (Compound [47])

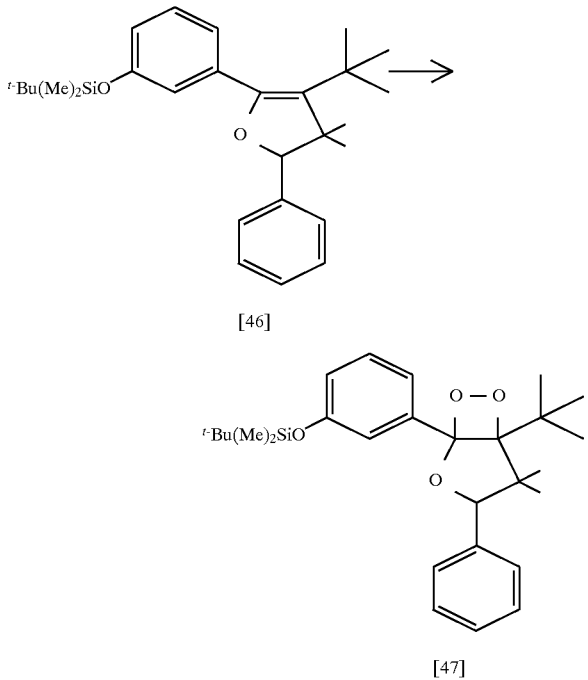

52.7 mg (0.121 mmol) of the compound [46] synthesized in Reference Example 33 and 0.5 mg of TPP were dissolved in 5 ml of dichloromethane, and the solution was stirred in an atmosphere of oxygen at −78° C.

This solution was irradiated with a sodium lamp (940 W) for 1 hour and 30 minutes. The reaction mixture was then concentrated.

The residue was subjected to preparative TLC and eluted with a mixed solvent of hexane and ethyl acetate (10:1), whereby 5-t-butyl-[3-(t-butyldimethylsiloxy)phenyl]-4,4-dimethyl-3-phenyl-2,6,7-trioxabicyclo[3.2.0]heptane (Compound [47]) was obtained in the form of a colorless oil in a yield of 48.5 mg (85.7%).

$^1$HNMR(400 MHz, CDCl$_3$): δ0.20 (s, 6H), 0.87 (s, 3H), 1.00 (s, 9H), 1.06 (s, 9H), 1.20 (s, 3H), 5.75 (s, 1H), 6.90 (dt, J=7.3 and 2.4 Hz, 1H), 7.21–7.45 (m, 8H)ppm

Test Example 1

1 mg of 5-t-butyl-4,4-dimethyl-1-(3'-phosphoryloxy)phenyl-2,6,7-trioxabicyclo[3.2.0]heptane disodium salt (Compound [29]) synthesized in Example 7 was dissolved in 0.35 ml of methanol-d$_4$.

The solution was heated to 60° C. in a constant temperature bath, and the $^1$HNMR thereof was measured at constant time intervals.

As a result, the half-life period of 5-t-butyl-4,4-dimethyl-1-(3'-phosphoryloxy)phenyl-2,6,7-trioxabicyclo[3.2.0]heptane disodium salt at 60° C. was estimated to be 17 hours.

For comparison, the half-life period of a commercially available AMPPD (3-(2'-spiroadamantan)-4-methoxy-(3"-phosphoryloxy)phenyl-1,2-dioxetane disodium salt) was measured under the same conditions as mentioned above.

The result was that the half-life period of the AMPPD at 60° C. was estimated to be 5 hours and 30 minutes.

Test Example 2

10 mg of 5-t-butyl-1-(3-methoxy)phenyl-4,4-dimethyl-2,6,7-trioxabicyclo[3.2.0]heptane (Compound [22]) synthesized in Example 5 was dissolved in 0.35 ml of p-xylene-d$_{10}$, and the solution was heated to 100° C. in a constant temperature bath, and the $^1$HNMR thereof was measured at constant time intervals.

The above procedure was repeated except that the solution was heated to 110° C. in a constant temperature bath, so that the $^1$HNMR thereof was measured at constant time intervals.

The above procedure was further repeated except that the solution was heated to 120° C. in a constant temperature bath, so that the $^1$HNMR thereof was measured at constant time intervals.

From the above measurements, the rate constant of the reaction at each temperature was calculated, from which the half-life period of 5-t-butyl-1-(3-methoxy)phenyl-4,4-dimethyl-2,6,7-trioxabicyclo[3.2.0]heptane (Compound [22]) at 25° C. was estimated to be 51.8 years.

Test Example 3

10 mg of 5-t-butyl-1-(3-t-butyldimethylsiloxy)phenyl-4,4-dimethyl-2,6,7-trioxabicyclo[3.2.0]heptane (Compound [25]) synthesized in Example 6 was dissolved in 0.35 ml of p-xylene-d$_{10}$, and the solution was heated to 80° C. in a constant temperature bath, and the $^1$HNMR thereof was measured at constant time intervals.

The above procedure was repeated except that the solution was heated to 100° C. in a constant temperature bath, so that the $^1$HNMR thereof was measured at constant time intervals.

The above procedure was repeated except that the solution was heated to 110° C. in a constant temperature bath, so that the $^1$HNMR thereof was measured at constant time intervals.

The above procedure was further repeated except that the solution was heated to 120° C. in a constant temperature bath, so that the $^1$HNMR thereof was measured at constant time intervals.

From the above measurements, the rate constant of the reaction at each temperature was calculated, from which the half-life period of 5-t-butyl-1-(3-t-butyldimethylsiloxy)phenyl-4,4-dimethyl-2,6,7-trioxabicyclo[3.2.0]heptane (Compound [25]) synthesized in Example 6 at 25° C. was estimated to be 20.4 years.

In contrast to this, the half-life period of 4-(3-t-butyldimethylsilyloxyphenyl)-4-methoxyspiro[1,2-dioxetane-3,2'-adamantan] at 25° C. is estimated to be 3.8 years (A. P. Schaap, et al., Tetrahedron Lett., 28, 1155 (1987)).

Test Example 4

10 mg of 5-isopropyl-1-(3-methoxy)phenyl-4,4-dimethyl-2,6,7-trioxabicyclo[3.2.0]heptane (Compound [11]) synthesized in Example 2 was dissolved in 0.35 ml of toluene-d$_8$, and the solution was heated to 80° C. in a constant temperature bath, and the $^1$HNMR thereof was measured at constant time intervals.

The above procedure was repeated except that the solution was heated to 90° C. in a constant temperature bath, so that the $^1$HNMR thereof was measured at constant time intervals.

The above procedure was repeated except that the solution was heated to 100° C. in a constant temperature bath, so that the $^1$HNMR thereof was measured at constant time intervals.

From the above measurements, the rate constant of the reaction at each temperature was calculated, from which the half-life period of 5-isopropyl-l-(3-methoxy)phenyl-4,4-dimethyl-2,6,7-trioxabicyclo[3.2.0]heptane (Compound [11]) synthesized in Example 2 at 25° C. was estimated to be 12.7 years.

Test Example 5

10 mg of 1-(3-t-butyldimethylsiloxy)phenyl-5-isopropyl-4,4-dimethyl-2,6,7-trioxabicyclo[3.2.0]heptane (Compound [14]) synthesized in Example 3 was dissolved in 0.35 ml of toluene-d$_8$, and the solution was heated to 80° C. in a constant temperature bath, and the $^1$HNMR thereof was measured at constant time intervals.

The above procedure was repeated except that the solution was heated to 90° C. in a constant temperature bath, so that the $^1$HNMR thereof was measured at constant time intervals.

The above procedure was repeated except that the solution was heated to 100° C. in a constant temperature bath, so that the $^1$HNMR thereof was measured at constant time intervals.

From the above measurements, the rate constant of the reaction at each temperature was calculated, from which the half-life period of 1-(3-t-butyldimethylsiloxy)phenyl-5-isopropyl-4,4-dimethyl-2,6,7-trioxabicyclo[3.2.0]heptane (Compound [14]) synthesized in Example 3 at 25° C. was estimated to be 7.0 years.

Test Example 6

10 mg of 3,5-di-t-butyl-1-[3-(t-butyldimethylsiloxy)phenyl]-4,4-dimethyl-2,6,7-trioxabicyclo[3.2.0]heptane (Compound [40]) synthesized in Example 10 was dissolved in 0.35 ml of p-xylene-d$_{10}$, and the solution was heated to 100° C. in a constant temperature bath, and the $^1$HNMR thereof was measured at constant time intervals.

The above procedure was repeated except that the solution was heated to 110° C. in a constant temperature bath, so that the $^1$HNMR thereof was measured at constant time intervals.

The above procedure was further repeated except that the solution was heated to 120° C. in a constant temperature bath, so that the $^1$HNMR thereof was measured at constant time intervals.

From the above measurements, the rate constant of the reaction at each temperature was calculated, from which the half-life period of 3,5-di-t-butyl-1-[3-(t-butyldimethylsiloxy)phenyl]-4,4-dimethyl-2,6,7-trioxabicyclo[3.2.0]heptane (Compound [40]) at 25° C. was estimated to be 247 years.

Test Example 7

10 mg of 5-t-butyl-1-(3-methoxyphenyl)-4,4-dimethyl-3-phenyl-2,6,7-trioxabicyclo[3.2.0]heptane (Compound [44]) synthesized in Example 11 was dissolved in 0.35 ml of p-xylene-d$_{10}$, and the solution was heated to 80° C. in a constant temperature bath, and the $^1$HNMR thereof was measured at constant time intervals.

The above procedure was repeated except that the solution was heated to 90° C. in a constant temperature bath, so that the $^1$HNMR thereof was measured at constant time intervals.

The above procedure was repeated except that the solution was heated to 100° C. in a constant temperature bath, so that the $^1$HNMR thereof was measured at constant time intervals.

The above procedure was further repeated except that the solution was heated to 110° C. in a constant temperature bath, so that the $^1$HNMR thereof was measured at constant time intervals.

From the above measurements, the rate constant of the reaction at each temperature was calculated, from which the half-life period of 5-t-butyl-1-(3-methoxyphenyl)-4,4-dimethyl-3-phenyl-2,6,7-trioxabicyclo[3.2.0]heptane (Compound [44]) at 25° C. was estimated to be 72 years.

Test Example 8

10 mg of 5-t-butyl-1-[3-(t-butyldimethylsiloxy)phenyl]-4,4-dimethyl-3-phenyl-2,6,7-trioxabicyclo[3.2.0]heptane (Compound [47]) synthesized in Example 12 was dissolved in 0.35 ml of p-xylene-d$_{10}$, and the solution was heated to 80° C. in a constant temperature bath, and the $^1$HNMR thereof was measured at constant time intervals.

The above procedure was repeated except that the solution was heated to 90° C. in a constant temperature bath, so that the $^1$HNMR thereof was measured at constant time intervals.

The above procedure was repeated except that the solution was heated to 100° C. in a constant temperature bath, so that the $^1$HNMR thereof was measured at constant time intervals.

The above procedure was further repeated except that the solution was heated to 110° C. in a constant temperature bath, so that the $^1$HNMR thereof was measured at constant time intervals.

From the above measurements, the rate constant of the reaction at each temperature was calculated, from which the half-life period of 5-t-butyl-1-[3-(t-butyldimethylsiloxy)phenyl]-4,4-dimethyl-3-phenyl-2,6,7-trioxabicyclo[3.2.0]heptane (Compound [47]) at 25° C. was estimated to be 52 years.

Test Example 9

5-t-butyl-4,4-dimethyl-1-(3'-phosphoryloxy)phenyl-2,6,7-trioxabicyclo[3.2.0]heptane disodium salt (Compound [29]) synthesized in Example 7 was dissolved in a 0.1M diethanolamine/hydrochloric acid buffer solution (pH 10.0) containing 1 mM magnesium chloride and 0.05% sodium azide, in such an amount that the concentration of the dissolved compound [29] was 0.2 mg/ml.

Furthermore, to the above solution, a quaternary ammonium salt TBQ was added in such an amount that the concentration of the added quaternary ammonium salt TBQ was 0.4 mg/ml. The above solution was then stirred.

300 μl of this solution was placed in a cartridge for assay and incubated for 15 minutes.

After this incubation, 20 μl of an enzyme solution with an enzyme concentration of 2.9×10$^{-12}$M was added to the above solution, which enzyme solution was prepared by diluting an alkaline phosphatase solution for enzyme immunoassay (made by Boehringer Mannheim Co., Ltd.) with a 50 mM Tris/Cl buffer solution (pH 7.2) containing 0.15M sodium chloride, 1 mM magnesium chloride, 0.1 mM zinc chloride and 0.1% sodium azide.

The above solution was stirred and the luminescence thereof was measured at 37° C. at constant time intervals.

For comparison, the luminescence of a commercially available AMPPD (3-(2'-spiroadamantan)-4-methoxy-4-(3"-phosphoryloxy)phenyl-1,2-dioxetane disodium salt) was measured under the same conditions as mentioned above, by replacing the Compound [29] with AMPPD in accordance with the above-mentioned procedure.

The results are shown in FIG. 1.

Test Example 10

1 ml of a $6.35 \times 10^{-6}$M DMSO solution of 1-(3-t-butyldimethylsiloxy)phenyl-5-isopropyl-4,4-dimethyl-2,6,7-trioxabicyclo[3.2.0]heptane (Compound [14]) synthesized in Example 3 was added to 2 ml of $1.0 \times 10^{-1}$M DMSO of tetrabutylammoniumfluoride at 25° C.

The luminescence of the mixture at that moment was measured by a fluorescence analyzer. The luminescent quantum efficiency at that moment was estimated to be 0.12, and the half-life of the luminescence was 6.7 seconds and λmax was 464 nm.

Test Example 11

1 ml of a $1.00 \times 10^{-5}$M DMSO solution of 3,5-di-t-butyl-1-[3-(t-butyldimethylsiloxy)phenyl]-4,4-dimethyl-2,6,7-trioxabicyclo[3.2.0]heptane (Compound [40]) synthesized in Example 10 was added to 2 ml of $1.0 \times 10^{-2}$M DMSO of tetrabutylammoniumfluoride at 25° C.

The luminescence of the mixture at that moment was measured by a fluorescence analyzer. The luminescent quantum efficiency at that moment was estimated to be 0.19, and the half-life of the luminescence was 26 seconds and λmax was 461 nm.

Test Example 12

1 ml of a $1.00 \times 10^{-5}$M DMSO solution of 5-t-butyl-1-[3-(t-butyldimethylsiloxy)phenyl]-4,4-dimethyl-3-phenyl-2,6,7-trioxabicyclo[3.2.0]heptane (Compound [47]) synthesized in Example 12 was added to 2 ml of $1.0 \times 10^{-2}$M DMSO of tetrabutylammoniumfluoride at 25° C.

The luminescence of the mixture at that moment was measured by a fluorescence analyzer. The luminescent quantum efficiency at that moment was estimated to be 0.13, and the half-life of the luminescence was 165 seconds and λmax was 458 nm.

Thus, the 1,2-dioxetane derivatives of general formula (I) of the present invention have extremely high thermal stability and therefore when preserving the same, no refrigeration is necessary, and there are no troubles with respect to, for instance, time adjustment and temperature control.

What is claimed is:

1. A compound having the structure:

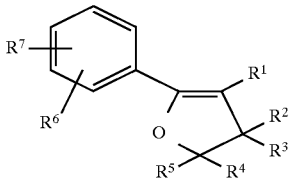

wherein $R^1$, $R^2$, $R^3$, $R^4$, and $R^5$ are each independently a hydrogen atom, an alkyl group or an aryl group, or wherein $R^2$ and $R^3$ together and $R^4$ and $R^5$ together are joined as a cycloalkyl group; wherein $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom, a halogen atom, an alkyl group, or an alkoxyl group.

2. The compound of claim 1, wherein $R^1$, $R^2$, $R^3$ are each independently an alkyl group, $R^4$ is an aryl group, $R^5$ is a hydrogen atom, $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom.

3. The compound of claim 1, wherein $R^1$, $R^2$, $R^3$ and $R^4$ are each independently an alkyl group, $R^5$ is a hydrogen atom, $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom.

4. The compound of claim 2, wherein $R^1$, $R^2$, $R^3$ are each independently an alkyl group having 1 to 4 carbon atoms, $R^4$ is a phenyl group; $R^5$ is a hydrogen atom, $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom.

5. The compound of claim 3, wherein $R^1$, $R^2$, $R^3$ and $R^4$ are each independently an alkyl group having 1 to 4 carbons, $R^5$ is a hydrogen atom, $R^6$ is a hydroxyl group, an alkoxyl group, an aralkyloxy group, or —OSi ($R^8$ $R^9$ $R^{10}$) in which $R^8$, $R^9$ and $R^{10}$ are each independently an alkyl group or a phosphate salt group and $R^7$ is a hydrogen atom.

6. The compound of claim 4, wherein $R^6$ is —OSi ($R^8$ $R^9$ $R^{10}$) in which $R^8$, $R^9$ and $R^{10}$ are each independently an alkyl group.

7. The compound of claim 6, wherein $R^8$, $R^9$ and $R^{10}$ are each independently an alkyl group having 1 to 4 carbons.

8. The compound of claim 4, wherein $R^6$ is a phosphate salt.

9. The compound of claim 4, wherein $R^6$ is an alkoxyl group.

10. The compound of claim 9, wherein $R^6$ is an alkoxyl group having 1 to 4 carbons.

11. The compound of claim 5, wherein $R^6$ is —OSi ($R^8$ $R^9$ $R^{10}$) in which $R^8$, $R^9$ and $R^{10}$ are each independently an alkyl group.

12. The compound of claim 11, wherein $R^8$, $R^9$ and $R^{10}$ are each independently an alkyl group having 1 to 4 carbons.

13. The compound of claim 5, wherein $R^6$ is a phosphate salt.

14. The compound of claim 5, wherein $R^6$ is an alkoxyl group.

15. The compound of claim 14, wherein $R^6$ is an alkoxyl group having 1 to 4 carbons.

* * * * *